(12) United States Patent
Boussiba et al.

(10) Patent No.: US 9,802,989 B2
(45) Date of Patent: Oct. 31, 2017

(54) OIL GLOBULE PROTEIN AND USES THEREOF

(75) Inventors: Sammy Boussiba, Omer (IL); Ehud Peled, Beer-Sheva (IL); Uri Pick, Nes Ziona (IL); Aliza Zarka, Beer-Sheva (IL); Stefan Lou, Beer-Sheva (IL); Meira Weiss, Rehovot (IL)

(73) Assignees: Ben Gurion University of the Negev Research and Development Authority, Beer Sheva (IL); Yeda Research and Development Co. Ltd. at the Weizmann Institute of Science, Rehovot (IL)

( * ) Notice: Subject to any disclaimer, the term of this patent is extended or adjusted under 35 U.S.C. 154(b) by 200 days.

(21) Appl. No.: 13/819,774

(22) PCT Filed: Aug. 30, 2011

(86) PCT No.: PCT/IL2011/000695
§ 371 (c)(1),
(2), (4) Date: Jun. 13, 2013

(87) PCT Pub. No.: WO2012/029060
PCT Pub. Date: Mar. 8, 2012

(65) Prior Publication Data
US 2015/0175671 A1    Jun. 25, 2015

Related U.S. Application Data

(60) Provisional application No. 61/378,008, filed on Aug. 30, 2010.

(51) Int. Cl.
C07K 14/40 (2006.01)
C07K 14/19 (2006.01)
C07K 14/405 (2006.01)
C07K 14/195 (2006.01)

(52) U.S. Cl.
CPC .......... *C07K 14/405* (2013.01); *C07K 14/195* (2013.01)

(58) Field of Classification Search
None
See application file for complete search history.

(56) References Cited

U.S. PATENT DOCUMENTS

| | | |
|---|---|---|
| 7,541,329 B2 | 6/2009 | Bringe et al. |
| 2008/0038774 A1 | 2/2008 | Higashiyama et al. |
| 2010/0008871 A1 | 1/2010 | Cunningham |

OTHER PUBLICATIONS

Merchant et al (The *Chlamydomonas* genome reveals the evolution of key animal and plant functions. Science 318:245-250, 2007).*

Merchant et al. The *Chlamydomonas* genome reveals the evolution of key animal and plant functions. Science 318:245-250(2007).
Kapchie et at, Evaluation of enzyme efficiency for soy oleosome isolation and ultrastructural aspects. Food Research International 43 (2010) 241-247.
Lamers et al, Exploring and exploiting carotenoid accumulation in Dunaliella salina for cell-factory applications. Trends in Biotechnology. vol. 26, Issue 11, Nov. 2008, pp. 631-638.
Brennan et aL Biofuels from microalgae, A review of technologies for production, processing, and extractions of biofuels and co-products. Renewable and Sustainable Energy Reviews 14 (2010) 557-577 p. 571, Table 1.
Peled et al. 'Isolation of a Novel Oil Globule Protein from the Green Alga *Haematococcus pluvialis* (Chlorophyceae).' Lipids vol. 46 p. 851-861; Jul. 6, 2011 (Jul. 6, 2011) Fig. 6, accession No. HQ213938.
Merchant et al., The *Chlamydonnonas genome* reveals the evolution of key animal and plant functions. Science 318:245-250(2007). depositied in UniProtKB/TrEMBL A8J816_CHLRE.
Kapchie et al. Evaluation of enzyme efficiency for soy oleosome isolation and ultrastructural aspects. Food Research International 43 (2010) 241-247 Abstract.
Lamers et al. Exploring and exploiting carotenoid accumulation in Dunaliella salina for cell-factory applications. Trends in Biotechnology, vol. 26, Issue 11, Nov. 2008, pp. 631-638 Abstract.
Brennan et al. Biofuels for microalgae, A review of technologies for production, processing, and extractions of biofuels and co-products. Renewable and Sustainable Energy Reviews 14 (2010) 557-577, p. 571, Table 1.
Peled et al. "Isolation of a Novel Oil Globule Protein form the Green Ala *Haematococcus pluvialis* (Chlorophyceae)". Lipids, vol. 46 p. 851-861; Jul. 6, 2011 (Jul. 6, 2011) Fig. 6, accession No. HQ213938.
PCT—Notification of Transmittal of the International Search Report and the Written Opinion of the International Searching Authority, or the Declaration—7 pages—dated Jun. 14, 2012.
SubName: Full=Putative uncharacterized protein;, XP002722314, retrieved from EBI accession No. UNIPROT: D8UJ18, database accession No. D8UJ18—last modified on Oct. 5, 2010 (3 pages).
SubName: Full=Oil Globule associated protein;, XP002722315, retrieved from EBI accession No. UNIPROT:E2JF04, database accession No. E2JF04—last modified on Nov. 30, 2010 (3 pages).
Haematococcus pluvialis culture-collection SCCAP:K-0084 oil globule associated protein mRNA, complete cds, XP002722316, retrieved from EBI accession No. EM_STD:HQ213938, database accession No. HQ213938—Oct. 4 2010 (2 pages).

* cited by examiner

*Primary Examiner* — Medina A Ibrahim
*Assistant Examiner* — Wayne Zhong
(74) *Attorney, Agent, or Firm* — Roach Brown McCarthy & Gruber, P.C.; Kevin D. McCarthy

(57) ABSTRACT

An isolated novel oil globule protein encoded by a polynucleotide sequence is provided together with a composition which includes the isolated protein. A transgenic organism transformed by a polynucleotide encoding a protein which at least partially comprises the amino acid sequence of the novel oil globule protein is also provided. The invention also provides a method for producing or enhancing the production of a carotenoid such as astaxanthin, which is an oil globule constituent.

11 Claims, 6 Drawing Sheets

```
           SEQ ID NO.
Polytomella    33  ---------------------------------------------------------      --
Haematococcus  34  MSE----KQLKRLGFVHQGASYAYSYTGTAEKLYKTARSFAPTFVEPTLAQVEDRVVAITA    57
Chlamydomonas  35  MAESAGKPLKHLEFVHTYAHKFASGAAYVEGGYQKAKTYVPAVAQPYIAKAEETCLAYAA    60
Volvox         36  MAD--DRKLKRLGFVDAYTHKLANGAAYVEGAYKKVKPLVPQQVQPFLAKVEDAVLAYTA    58
                          : .  **:*. *. . : .  * *:. : . . . . . . : * . :*

Polytomella        ------NAQDKAEKILKKADDQVDKVVSNAHNIYQAGRSYDYAVNIMEIHQNNIETYQQT    56
Haematococcus      PVVAQAQDLSEKALHIADDQVECIVNTTDKAVADGKKGVVDCMKVEMHEKNMQTYIAT     117
Chlamydomonas      PLATKATDHAEKILRSTDAQLDALYAASASWLSSSQK---------LADSNIAAFRGA    109
Volvox             PVVAKASDQAEKFLRITDEQVDYLYVETAAYLTQTRK---------------LTQSNIDTFRSA   107
                    . . :: * .:.:: .*.* :                                *

Polytomella        THKYFQLVSSTAEWVAARVAPTQAFQKAHEILRLSLNKAQECADPDKAVKIVDSWVVFS    116
Haematococcus      SNRYFEYIKGMSEWAKDKMNPIKGGQHALDTLNAAIAKAQEATDPDVAAKMALDAWNSFA    177
Chlamydomonas      ADKYYDLVKSTAQHVTSKLPTDLSVAKARELLSASLEQAKALADPDAAVAAALDAWTKFA    169
Volvox             ADKYYQMVKSTADYLASKLSYDISVQAARDFISKSVEKAKELSDPDAAVRIVYDSWQQFA    167
                    :. * :  .:: .  .                  *   * .  .*

Polytomella        SVPVVASVLPYLEPAAARAFQNFRSIHDSLVVSPHYKQGYDMASATLQWATTTSPFRLGA    176
Haematococcus      SVPVVAKVLETADPVTQTGLSSFYKLHDTILVSWPLLYSKVVSTGVSTLSWATTTMPYKLGA    237
Chlamydomonas      AIPAVAKVLSAASPLTGKGVAAFTAAAHDLLVHSALYRGVSVSLGASTLGWATSTTPYKLSA    229
Volvox             AIPAVAKTLEKTAPVTRKGFETFIAAAHDALVSSLVYKRSVSLGATTLGWATTTPYKLGA    227
                   : :** ..:    . . *  :*    **:* .  :     ::*:* ****.* **:.*

Polytomella        NVM---------------------------------------------------------    179
Haematococcus      QYMYPLVQPVADPALAKITNSKVINGTLSYWKPTASAA---------------------    275
Chlamydomonas      AYLYPLVQPVADPALDKVSKSTYVNAAIKYWAPAPVAAA--------------------    268
Volvox             QYLYPMVQSVADPAL--------------------------------------------    242
                    :*::**:.:******   .*:: :* . ::** *

Figure 6
```

OIL GLOBULE PROTEIN AND USES THEREOF

FIELD OF INVENTION

This invention is directed to, inter alia, an oil globule protein, isolated polynucleotide molecules encoding the same, and methods of making and utilizing the same.

BACKGROUND OF THE INVENTION

Oil globules are discrete sub-cellular organelles surrounded by a monolayer of amphipathic phospholipids, glycolipids or sterols that encircle a hydrophobic core of neutral lipids. They are ubiquitous in animals, micro-organisms and plants. In many micro-organisms, such as yeasts, microalgae and bacteria, the accumulation of oil globules appears to be induced specifically in response to environmental stresses such as nutrient limitation, high radiation or osmotic stress (Murphy D. (2001), Prog Lipid Res 40:325-438; Zhekisheva et al., (2005), J Phycol 41:819-826). Different models for oil globule biogenesis were postulated and are still in debate. Nevertheless it is commonly accepted that globules arise by vesiculation from the ER (Walther and Farese Jr., (2009), Biochim Biophys Acta Mol Cell Biol Lipids 1791:459-466).

Plant oil globules contain specific populations of proteins that are more or less tightly bound to their surface. Globule proteins described in the literature were suggested to play different roles, including globule formation, degradation, stabilization and globule-globule or globule-other organelles interaction. In *Drosophila*, yeast and mammalians, globules were also shown to compose refugee proteins which are not directly linked to lipid metabolism. Oleosin is the most abundant oil-body-associated protein family identified in plants but until today it has not been found in algae. Caleosin, a calcium binding lipid-body protein that was found to be associated also with ER membranes, is ubiquitous among higher plants.

Some unicellular algae are known to be able to deposit very large amounts of oil in oil globules. Oil accumulation is usually accompanied by cessation of cell growth and in some species oil can account for as high as 60% of the cell dry mass. To date little is known about algal oil globules and especially about their protein composition and their potential roles.

The unicellular green alga *Haematococcus pluvialis* is well known as the best natural source for the high value red pigment astaxanthin. This carotenoid is accumulated in cytoplasmic oil globules, under inductive conditions. Accumulation of astaxanthin in *H. pluvialis* is positively correlated with lipid accumulation; the former depends on the latter but not vise-versa. Lipids accumulation also depends on de novo fatty acid synthesis. Under nitrate deprivation astaxanthin and fatty acid content can reach up to 4% and 40% of cell dry mass, respectively. The build up of oil globules in *H. pluvialis* was also found to be structurally related to ER membranes.

SUMMARY OF THE INVENTION

The present invention provides a novel oil globule protein (OGP), which is enriched in isolated globules and stressed *H. pluvialis* cells, in correlation with accumulation of astaxanthin in the cells, and is found only in micro-algal cells. It is now disclosed for the first time that OGP gene transcription is barely detected in non stressed cells but is highly induced in stressed cells and in correlation to astaxanthin accumulation The present invention further provides globule protein profile of *H. pluvialis*, as obtained after globule isolation, as well as the total homogenate protein profile of the *H. pluvialis* cells over 14 days of astaxanthin accumulation. Further provided are compositions comprising the isolated oil globule protein or polynucleotides encoding the same, as well as methods of their making and uses thereof.

In one embodiment, the present invention provides an isolated protein comprising an amino acid sequence set forth in SEQ ID NO: 1 (Oil globule protein amino acid sequence).

In another embodiment, the present invention further provides a transgenic organism or a transformed bacteria transformed by a polynucleotide encoding a protein comprising an amino acid sequence set forth in SEQ ID NO: 1.

In another embodiment, the present invention further provides a cell comprising an expression vector encoding a protein comprising an amino acid sequence set forth in SEQ ID NO: 1.

In another embodiment, the present invention further provides a method of enhancing production of oil globules in a cell comprising the step of transforming a cell with a polynucleotide encoding a protein comprising an amino acid sequence set forth in SEQ ID NO: 1.

In another embodiment, the present invention further provides a method of enhancing a production of astaxanthin in a cell comprising the step of transforming a cell with a polynucleotide encoding a protein comprising an amino acid sequence set forth in SEQ ID NO: 1 and subjecting the cell to conditions which induce oil globules or astaxanthin production. In another embodiment, astaxanthin is astaxanthin ester.

In another embodiment, the present invention further provides a method of enhancing production of astaxanthin in a *Haematococcus pluvialis* cell comprising the steps of: (a) transforming the cell with a polynucleotide encoding a protein comprising an amino acid sequence set forth in SEQ ID NO: 1 under the control of an inducible promoter; growing the cell under proliferation promoting conditions; depriving the cell of nutrients; and exposing the cell to intense light; thereby enhancing a production of astaxanthin in a *Haematococcus pluvialis* cell

BRIEF DESCRIPTION OF THE DRAWINGS

FIG. 6: Multiple sequence alignment of *H. pluvialis* OGP protein with putative green algal orthologs from *C. rein-* hardtii (XP_001697668), *Volvox carteri f. Nagariensis* (FD812477) and *Polytomella parva* (EC748417). Insert is shadowed. Region of misalignment in hydropathy plot is underlined. Symbols: identical (*), conserved (:), semi-conserved (.).

Figure 7:
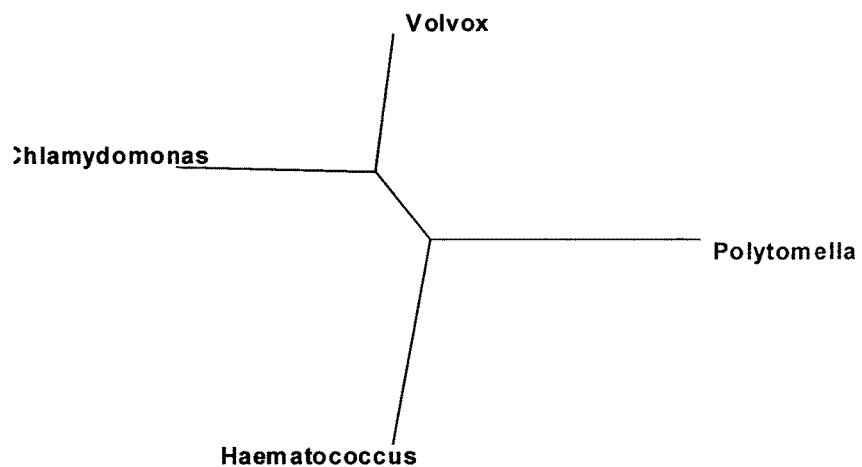

FIG. 7: Neighbor-joining phylogram of OGP and putative green microalgae orthologs.

Figure 8:
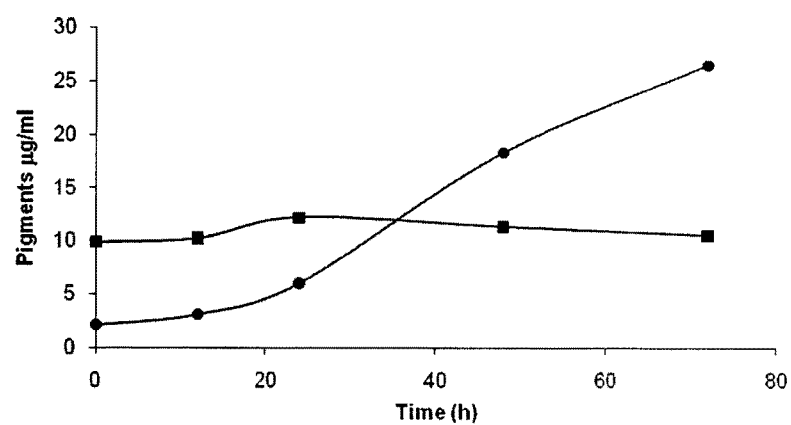

FIG. 8: A graph showing the changes in chlorophyll (■) and astaxanthin (●) contents during 72 h of oil globule accumulation inductive conditions in axenic cultures.

Figure 9:
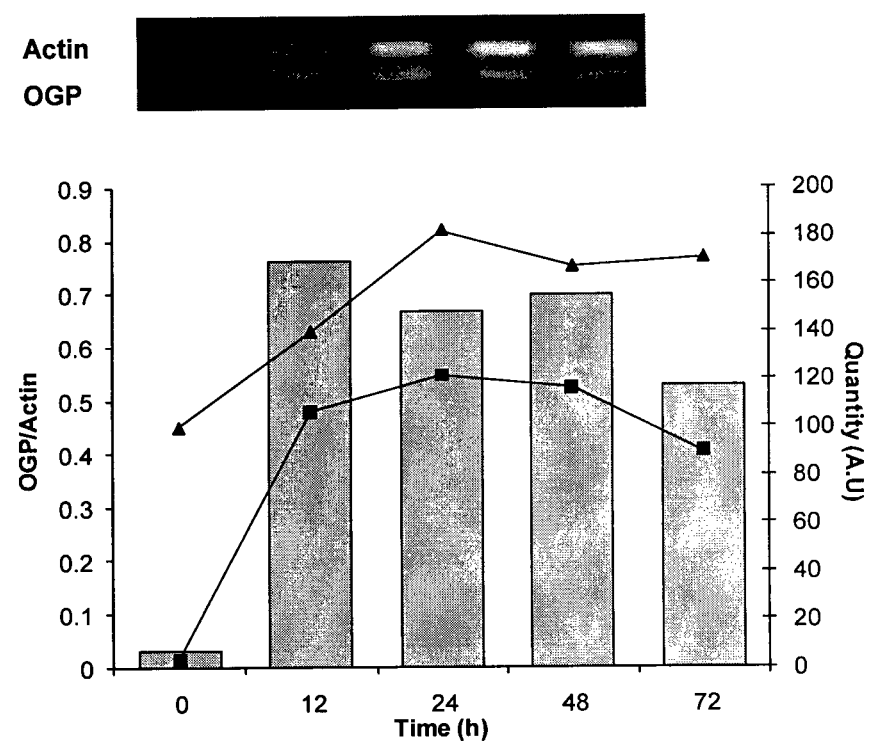

FIG. 9: Transcripts levels of actin ♦ and OGP gene ■ during 72 h of oil globule accumulation inductive conditions. PCR product on agarose gel and densitometric representation.

DETAILED DESCRIPTION OF THE INVENTION

In one embodiment, the present invention provides an isolated oil globule protein (OGP). In another embodiment, the present invention provides that the isolated oil globule protein is a microalgal oil globule protein. In another embodiment, the present invention provides that the isolated oil globule protein is a *H. pluvialis* oil globule protein.

In another embodiment, the present invention provides an OGP comprising or consisting the amino acid sequence:

(SEQ ID NO: 1)
MSEKQLKRLGFVHQGASYAYSYTGTAEKLYKTARSFAPTFVEPTLAQVED

RVVAITAPVVAQAQDLSEKALHIADDQVECIVNTTDKAVADGKKGVIDCM

NGVKEMHEKNMQTYIATSNRYFEYIKGMSEWAKDKMNPIKGGQHALDTLN

AAIAKAQEATDPDVAAKMALDAWNSFASVPVVAKVLETADPVTQTGLSSF

YKLHDTLVSWPLYSKVVSTGVSTLSWATTTMPYKLGAQYMYPLVQPVADP

ALAKITNSKVINGTLSYWKPTASAA.

In another embodiment, the OGP of the present invention comprises an amino acid sequence that is at least 50% homologous to the amino acid sequence of SEQ ID NO: 1. In another embodiment, the OGP of the present invention comprises an amino acid sequence that is at least 60% homologous to the amino acid sequence of SEQ ID NO: 1. In another embodiment, the OGP of the present invention comprises an amino acid sequence that is at least 70% homologous to the amino acid sequence of SEQ ID NO: 1. In another embodiment, the OGP of the present invention comprises an amino acid sequence that is at least 80% homologous to the amino acid sequence of SEQ ID NO: 1. In another embodiment, the OGP of the present invention comprises an amino acid sequence that is at least 85% homologous to the amino acid sequence of SEQ ID NO: 1. In another embodiment, the OGP of the present invention comprises an amino acid sequence that is at least 90% homologous to the amino acid sequence of SEQ ID NO: 1. In another embodiment, the OGP of the present invention comprises an amino acid sequence that is at least 95% homologous to the amino acid sequence of SEQ ID NO: 1. In another embodiment, the OGP of the present invention comprises an amino acid sequence that is at least 99% homologous to the amino acid sequence of SEQ ID NO: 1.

In another embodiment, the OGP of the present invention comprises an amino acid sequence that is at least 50% identical to the amino acid sequence of SEQ ID NO: 1. In another embodiment, the OGP of the present invention comprises an amino acid sequence that is at least 60% identical to the amino acid sequence of SEQ ID NO: 1. In another embodiment, the OGP of the present invention comprises an amino acid sequence that is at least 70% identical to the amino acid sequence of SEQ ID NO: 1. In another embodiment, the OGP of the present invention comprises an amino acid sequence that is at least 80% identical to the amino acid sequence of SEQ ID NO: 1. In another embodiment, the OGP of the present invention comprises an amino acid sequence that is at least 85% identical to the amino acid sequence of SEQ ID NO: 1. In another embodiment, the OGP of the present invention comprises an amino acid sequence that is at least 90% identical to the amino acid sequence of SEQ ID NO: 1. In another embodiment, the OGP of the present invention comprises an amino acid sequence that is at least 95% identical to the amino acid sequence of SEQ ID NO: 1. In another embodiment, the OGP of the present invention comprises an amino acid sequence that is at least 99% identical to the amino acid sequence of SEQ ID NO: 1.

In another embodiment, the OGP as described herein comprises at least a portion of the amino acid shown in SEQ ID. NO: 1. In another embodiment, the OGP as described herein is a variant of SEQ ID. NO: 1. In another embodiment, the term "variant" in relation to a certain sequence means a protein or a polypeptide which is derived from the sequence through the insertion or deletion of one or more amino acid residues or the substitution of one or more amino acid residues with amino acid residues having similar properties, e.g., the replacement of a polar amino acid residue with another polar amino acid residue, or the replacement of a non-polar amino acid residue with another non-polar amino acid residue. In all cases, variants must have an OGP function as defined herein.

In another embodiment, the OGP as described herein further comprises a leader peptide. In another embodiment, the leader peptide allows the polypeptide to be specifically located or targeted to a target organelle within the cell such as an oil globule.

In another embodiment, the present invention provides an isolated OGP. In another embodiment, the present invention provides an isolated polypeptide comprising a functional OGP. In another embodiment, the present invention provides that the polypeptide has the function of an OGP.

In another embodiment, the present invention provides an isolated polynucleotide encoding the protein as described herein. In another embodiment, an isolated polynucleotide is an isolated DNA molecule. In another embodiment, an isolated polynucleotide is an isolated cDNA molecule. In another embodiment, the isolated polynucleotide comprises a sequence encoding the protein as described herein. In another embodiment, the isolated polynucleotide comprises a DNA sequence encoding an OGP as described herein. In another embodiment, the isolated polynucleotide comprises a DNA sequence encoding a polypeptide comprising an OGP activity. In another embodiment, the isolated polynucleotide comprises a DNA sequence encoding a polypeptide consisting of an OGP activity.

In another embodiment, the isolated polynucleotide comprises a DNA sequence comprising or consisting the sequence:

(SEQ ID NO: 2)
ATGTCAGAGAAGCAGCTGAAGCGCTTGGGCTTCGTGCATCAGGGAGCCAG

CTATGCATACAGCTACACCGGCACAGCCGAGAAACTGTACAAGACAGCGC

GCTCCTTCGCCCCAACCTTTGTGGAACCCACCTTGGCCCAGGTTGAGGAT

CGCGTTGTGGCCATCACAGCCCCAGTGGTAGCCCAAGCGCAAGACCTCAG

-continued
CGAGAAGGCGTTACACATCGCCGATGACCAGGTGGACTGCATCCTGAACA

CCACCGACAAGGCGGTGGCAGACGGGAAGAAGGGCGTAGTTGATTGCATG

AACGGCGTGAAGGAGATGCACGAGAAGAACATGCAAACCTACATCGCCAC

GAGCAACAGCTACTTTGAGTACATCAAGGGCATCTCCGACTGGGCAAAAG

ATAAGCTGAACCCAATTAAGGGCGGCCAGCACGCCCTGGACACCCTGAAC

GCCGCGATTGCCAAGGCTCAAGAGGCAACTGACCCCGACGTGGCAGCTAA

GATGGCTCTGGATGCCTGGAACAGCTTTGCATCCGTGCCTGTGGTGGCCA

AGGTACTAGAGACAGCCGACCCAGTCACGCAGACCGGCCTGTCTTCCTTC

TACAAGCTGCACGACACCCTGGTGAGCTGGCCCCTGTACAGCAAGGTGGT

GTCGACCGGGGTGTCCACCCTGAGCTGGGCCACAACCACCACGCCCTACA

AGCTGGGCGCCCAGTACATGTACCCCCTGGTGCAGCCCGTGGCTGACCCA

GCATTGGCCAAGATCACCAACAGCAAGGTCATCAATGGCACGCTGTCGTA

CTGGAAGCCAACTGCCTCGGCAGCTTGA.

In another embodiment, the isolated polynucleotide comprises a DNA sequence comprising or consisting the sequence:

(SEQ ID NO: 3)
ACACATTTATTCAGCCAAATGTCAGAGAAGCAGCTGAAGCGCTTGGGCTT

CGTGCATCAGGGAGCCAGCTATGCATACAGCTACACCGGCACAGCCGAGA

AACTGTACAAGACAGCGCGCTCCTTCGCCCCAACCTTTGTGGAACCCACC

TTGGCCCAGGTTGAGGATCGCGTTGTGGCCATCACAGCCCCAGTGGTAGC

CCAAGCGCAAGACCTCAGCGAGAAGGCGTTACACATCGCCGATGACCAGG

TGGACTGCATCCTGAACACCACCGACAAGGCGGTGGCAGACGGGAAGAAG

GGCGTAGTTGATTGCATGAACGGCGTGAAGGAGATGCACGAGAAGAACAT

GCAAACCTACATCGCCACGAGCAACAGCTACTTTGAGTACATCAAGGGCA

TCTCCGACTGGGCAAAAGATAAGCTGAACCCAATTAAGGGCGGCCAGCAC

GCCCTGGACACCCTGAACGCCGCGATTGCCAAGGCTCAAGAGGCAACTGA

CCCCGACGTGGCAGCTAAGATGGCTCTGGATGCCTGGAACAGCTTTGCAT

CCGTGCCTGTGGTGGCCAAGGTACTAGAGACAGCCGACCCAGTCACGCAG

ACCGGCCTGTCTTCCTTCTACAAGCTGCACGACACCCTGGTGAGCTGGCC

CCTGTACAGCAAGGTGGTGTCGACCGGGGTGTCCACCCTGAGCTGGGCCA

CAACCACCACGCCCTACAAGCTGGGCGCCCAGTACATGTACCCCCTGGTG

CAGCCCGTGGCTGACCCAGCATTGGCCAAGATCACCAACAGCAAGGTCAT

CAATGGCACGCTGTCGTACTGGAAGCCAACTGCCTCGGCAGCTTGAGCTC

TGGTGCCAGGACCTACCCACAGCNGCAGGGATAGCAGCCNCATCAGGCAC

AGTCACGGCA.

In another embodiment, an OGP as described herein comprises a nucleic acid sequence that is at least 50% homologous to the nucleic acid sequence of SEQ ID NO: 2 or SEQ ID NO: 3. In another embodiment, an OGP of the present invention comprises a nucleic acid sequence that is at least 60% homologous to the nucleic acid sequence of SEQ ID NO: 2 or SEQ ID NO: 3. In another embodiment, an OGP of the present invention comprises a nucleic acid sequence that is at least 70% homologous to the nucleic acid sequence of SEQ ID NO: 2 or SEQ ID NO: 3. In another embodiment, an OGP of the present invention comprises a nucleic acid sequence that is at least 80% homologous to the nucleic acid sequence of SEQ ID NO: 2 or SEQ ID NO: 3. In another embodiment, an OGP of the present invention comprises a nucleic acid sequence that is at least 85% homologous to the nucleic acid sequence of SEQ ID NO: 2 or SEQ ID NO: 3. In another embodiment, an OGP of the present invention comprises a nucleic acid sequence that is at least 90% homologous to the nucleic acid sequence of SEQ ID NO: 2 or SEQ ID NO: 3. In another embodiment, an OGP of the present invention comprises a nucleic acid sequence that is at least 95% homologous to the nucleic acid sequence of SEQ ID NO: 2 or SEQ ID NO: 3. In another embodiment, an OGP of the present invention comprises a nucleic acid sequence that is at least 99% homologous to the nucleic acid sequence of SEQ ID NO: 2 or SEQ ID NO: 3.

In another embodiment, an OGP of the present invention comprises a nucleic acid sequence that is at least 50% identical to the nucleic acid sequence of SEQ ID NO: 2 or SEQ ID NO: 3. In another embodiment, an OGP of the present invention comprises a nucleic acid sequence that is at least 60% identical to the nucleic acid sequence of SEQ ID NO: 2 or SEQ ID NO: 3. In another embodiment, an OGP of the present invention comprises a nucleic acid that is at least 70% identical to the nucleic acid sequence of SEQ ID NO: 2 or SEQ ID NO: 3. In another embodiment, an OGP of the present invention comprises a nucleic acid sequence that is at least 80% identical to the nucleic acid sequence of SEQ ID NO: 2 or SEQ ID NO: 3. In another embodiment, an OGP of the present invention comprises a nucleic acid sequence that is at least 85% identical to the nucleic acid sequence of SEQ ID NO: 2 or SEQ ID NO: 3. In another embodiment, an OGP of the present invention comprises a nucleic acid sequence that is at least 90% identical to the nucleic acid sequence of SEQ ID NO: 2 or SEQ ID NO: 3. In another embodiment, an OGP of the present invention comprises a nucleic acid sequence that is at least 95% identical to the nucleic acid sequence of SEQ ID NO: 2 or SEQ ID NO: 3. In another embodiment, an OGP of the present invention comprises a nucleic acid sequence that is at least 99% identical to the nucleic acid sequence of SEQ ID NO: 2 or SEQ ID NO: 3.

In another embodiment, the present invention comprises an OGP or a nucleic acid molecule encoding the same combined with additional proteins and/or enzymes and/or substrates that are involved in the biosynthesis of an oil globule. In another embodiment, the present invention comprises an OGP or a nucleic acid molecule encoding the same combined with additional proteins and/or enzymes and/or substrates that are involved in the biosynthesis of carotenoids such as but not limited to astaxanthin or esters thereof. In another embodiment, the present invention comprises an OGP or a nucleic acid molecule encoding the same combined with additional proteins and/or enzymes and/or substrates that are involved in the biosynthesis of H. pluvialis oil globules and/or astaxanthin. In another embodiment, the present invention comprises a method of producing astaxanthin in a plant cell or an alga cell comprising transiently or constitutively expressing OGP in the cell. In another embodiment, the present invention comprises a method of enhancing the production of astaxanthin in a plant cell or an alga cell comprising transiently or constitutively expressing OGP in the cell.

In another embodiment, carotenoid is a plant carotenoid or a heterotrophic microorganism carotenoid. In another embodiment, astaxanthin is a plant astaxanthin. In another embodiment, astaxanthin is an algal astaxanthin. In another embodiment, astaxanthin is a *H. pluvialis* astaxanthin. In another embodiment, carotenoid of the invention is produced in or by an animal cell. In another embodiment, carotenoid of the invention is produced in or by a marine organism. In another embodiment, astaxanthin of the invention is produced in or by a plant or a plant cell.

In another embodiment, astaxanthin is an antioxidant. In another embodiment the free radical scavenging activity of astaxanthin protects lipids from peroxidation and reduces oxidative damage of LDL-cholesterol (thereby reducing arterial plaque formation), cells, cell membranes, and mitochondrial membranes.

In another embodiment, astaxanthin supplementation strengthens the immune system by increasing the number of antibody producing cells. In another embodiment, astaxanthin enhances antibody production by exerting its activity on T-cells and T-helper cells. In another embodiment, astaxanthin is effective in the treatment of neurodegenerative conditions such as but not limited to Alzheimer's and Parkinson disease. In another embodiment, astaxanthin protects the eyes and skin from sun radiation damage by quenching singlet and triplet oxygen. In another embodiment, astaxanthin reduces retinal injury. In another embodiment, astaxanthin is effective in the treatment of cancer. In another embodiment, astaxanthin is 3,3'-Dihydroxy-b,b-carotene-4,4'-dione.

In another embodiment, the present invention comprises a composition comprising an OGP as described herein or a nucleic acid molecule encoding the same. In another embodiment, the present invention comprises a composition comprising astaxanthin produced by a cell transformed or transfected with an OGP as described herein. In another embodiment, the present invention includes a composition comprising a fatty acid produced by a cell transformed or transfected with an OGP as described herein. In another embodiment, the present invention includes a composition comprising oil produced in an oil globule in a cell transformed or transfected with an OGP as described herein. In another embodiment, the present invention comprises a composition comprising astaxanthin or any other constituent of an oil globule produced by a transgenic or transformed organism comprising a polynucleotide molecule encoding the OGP as described herein. In another embodiment, the present invention comprises a composition comprising an OGP as described herein or a nucleic acid molecule encoding the same combined with additional proteins and/or enzymes and/or substrates that are involved in the biosynthesis of oil globules and/or astaxanthin. In another embodiment, the present invention comprises a composition comprising a cell transfected or transformed by a nucleic acid molecule encoding an OGP as described herein. In another embodiment, the cell is a prokaryotic cell. In another embodiment, the cell is an eukaryotic cell. In another embodiment, the cell is a plant cell. In another embodiment, the cell is an algal cell.

In another embodiment, provided herein a transgenic organism transformed by a polynucleotide of the invention. In another embodiment, the organism is a plant. In another embodiment, the organism is a seed. In another embodiment, the organism is an alga. In another embodiment, the organism is a microalga. In another embodiment, provided herein a seed or an offspring of a transgenic organism as described herein wherein the seed or offspring expresses an OGP as described herein.

In another embodiment, the present invention comprises an OGP transgenic plant or an OGP transformed bacteria. In another embodiment, the present invention comprises an OGP transgenic microalga or alga. In another embodiment, the present invention comprises an OGP transgenic plant or an OGP transformed bacteria combined with additional enzymes and/or substrates that are involved in the biosynthesis of oil globules, fatty acids, and/or astaxanthin.

In another embodiment, the present invention comprises a *H. pluvialis* over-expressing an OGP as described herein. In another embodiment, the present invention comprises a cell or an organism over-expressing an OGP. In another embodiment, the present invention comprises a cell or an organism over-expressing an endogenic or exogenic OGP. In another embodiment, the present invention provides that over-expression of an OGP results in hyper production of oil globules. In another embodiment, the present invention provides that over-expression of an OGP results in hyper production astaxanthin.

In another embodiment, a genetically engineered organism and/or *H. pluvialis* as described herein is transformed with a vector comprising a polynucleotide molecule encoding an OGP under the control of a constitutively active promoter. In another embodiment, a genetically engineered organism and/or *H. pluvialis* as described herein is transformed with a vector comprising a polynucleotide molecule encoding a self OGP under the control of a constitutively active promoter. In another embodiment, *H. pluvialis* is transformed with a vector comprising a polynucleotide molecule encoding a self OGP under the control of a constitutively active promoter. In another embodiment, *H. pluvialis* is transformed with a vector comprising the polynucleotide molecule of SEQ ID NO: 2 or SEQ ID NO: 3 under the control of a constitutively active promoter. In another embodiment, *H. pluvialis* is transformed with a vector comprising a polynucleotide molecule encoding the protein comprising or consisting of the amino acid sequence SEQ ID NO: 1, under the control of a constitutively active promoter. In another embodiment, an alga or microalga as described is transformed according to the methods described in EP1789530 which is hereby incorporated herein by reference in its entirety. In another embodiment, the methods described in EP1789530 are used for the introduction of an endogenous OGP (such as the one encoded by SEQ ID NO: 2 or SEQ ID NO: 3) into competent microalgae cells, thereby over-expressing OGP and enhancing the biogenesis of oil globules within the transfected cells. In another embodiment, over-expressing OGP in *H. pluvialis* results in increased number of oil globules. In another embodiment, over-expressing OGP in *H. pluvialis* results in increased number of oil globules comprising astaxanthin. In another embodiment, over-expressing OGP in *H. pluvialis* results in increased amount of astaxanthin in an oil globule.

In another embodiment, the expression of an OGP as described herein is controlled by a cell specific promoter. In another embodiment, the expression of an OGP as described herein is controlled by a plant promoter. In another embodiment, the expression of an OGP as described herein is controlled by an algal promoter. In another embodiment, the expression of an OGP as described herein is controlled by a bacterial promoter. In another embodiment, the expression of an OGP as described herein is controlled by a viral promoter.

In another embodiment, the expression of an OGP as described herein is controlled by a constitutive promoter. In another embodiment, the expression of an OGP as described herein is controlled by a constitutive promoter whose expression is independent of environmental and/or developmental factors. In another embodiment, the expression of an OGP as described herein is controlled by a constitutive promoter whose expression is independent of endogenous factors.

In another embodiment, the expression of an OGP as described herein is controlled by a tissue-specific or development-stage-specific promoter. In another embodiment, the expression of an OGP as described herein is controlled by a promoter element that is expressed or affect the expression of genes in the vascular system, photosynthetic tissues, tubers, roots and/or other vegetative organs, or seeds and/or other reproductive organs.

In another embodiment, the expression of an OGP as described herein is controlled by an inducible promoter. In another embodiment, the expression of an OGP as described herein is controlled by an inducible promoter conditioned to environmental conditions and external stimuli that can be artificially controlled. In another embodiment, the expression of an OGP as described herein is controlled by an inducible promoter conditioned to an abiotic factor such as light, oxygen levels, heat, cold and wounding. In another embodiment, the expression of an OGP as described herein is controlled by an inducible promoter conditioned to a chemical compound, not found naturally in the organism of interest. In another embodiment, the expression of an OGP as described herein is controlled by an inducible promoter conditioned to an antibiotic, copper, alcohol, steroids, and/or herbicides, among other compounds.

In another embodiment, the expression of an OGP as described herein is controlled by a synthetic promoter. In another embodiment, a synthetic promoter is made by bringing together the primary elements of a promoter region from diverse origins.

In another embodiment, the expression of an OGP as described herein is controlled by a regulatory expression system based on transactivating proteins. In another embodiment, a regulatory expression system regulates the expression of genes of interest irrespective of their physical position to the target genes.

In another embodiment, a vector is used according to the cell or organism utilized. In another embodiment, bacterial, algal, plant, and animal cell vectors are readily available to one of average skill in the art. In another embodiment, vector control elements are used according to the cell, organism, or tissue utilized. In another embodiment, bacterial, plant, and animal cell vector control elements are readily available to one of average skill in the art. In another embodiment, vector control elements comprise an origin of replication and a promoter.

In another embodiment, the present invention provides a composition comprising a vector comprising the polynucleotide as described herein. In another embodiment, the present invention provides a composition comprising a vector comprising a polynucleotide encoding an OGP as described herein.

In another embodiment, one of skill in the art can readily prepare a composition as described herein. In another embodiment, one of skill in the art can readily prepare a composition comprising a polynucleotide as described herein. In another embodiment, one of skill can readily prepare a composition comprising a combination of polynucleotides, plasmids, vectors etc. as described herein. In another embodiment, the present invention provides a composition comprising the OGP as described herein to be used in industrial applications for the manufacturing of oil globules and/or oil globules constituents such as but not limited to astaxanthin. In another embodiment, a composition as described herein is a kit comprising the components for the in vitro manufacturing of astaxanthin.

In another embodiment, provided herein a method of producing an oil globule and/or carotenoid in a cell comprising the step of transforming or transfecting a cell with a polynucleotide as described herein, thereby producing an oil globule and/or astaxanthin in a cell. In another embodiment, the cell is a eukaryotic cell. In another embodiment, the cell is a plant cell. In another embodiment, the cell is an animal cell. In another embodiment, the cell is a prokaryotic cell. In another embodiment, the cell is an algal cell. In another embodiment, the cell is a bacterial cell. In another embodiment, the cell is a *H. pluvialis* cell.

In another embodiment, provided herein a method for increasing oil and/or polyunsaturated fatty acid (PUFA) and/or a carotenoid content in a cell, comprising the step of over expressing a polynucleotide sequence encoding an OGP in a cell. In another embodiment, provided herein a method for increasing an oil globule and/or a carotenoid content in a cell, comprising the step of over expressing a polynucleotide sequence encoding an OGP in a cell, thereby increasing oil globule and/or carotenoid content in a cell. In another embodiment, the cell is a microalga cell or a prokaryotic cell. In another embodiment, the cell is a plant cell. In another embodiment, the cell is any cell. In another embodiment, methods for over-expressing or de-novo expressing a protein encoded by a vector such as a plasmid are known to one of average skill in the art.

In another embodiment, provided herein a method for increasing an oil globule and/or a carotenoid content in a heterotrophic microorganism cell, comprising the step of over expressing a polynucleotide sequence encoding an OGP in the cell. In another embodiment, provided herein a method for increasing oil content in a heterotrophic microorganism cell, comprising the step of over expressing a polynucleotide sequence encoding an OGP. In another embodiment, provided herein a method for increasing PUFA content in a heterotrophic microorganism cell, comprising the step of over expressing a polynucleotide sequence encoding an OGP. In another embodiment, heterotrophic microorganisms include but are not limited to fungi, dinoflagellates. In another embodiment, a heterotrophic microorganism is utilized as an industrial source for oil and/or carotenoids.

In another embodiment, over expressing a polynucleotide sequence encoding a self (endogenous) OGP or an exogenous OGP in a cell, results according to the methods of the present invention in enhancement of the production of oil and/or PUFA in a cell. In another embodiment, cells or organisms of the invention that over express a polynucleotide sequence encoding a self (endogenous) OGP or an exogenous OGP which results in enhancement of oil and/or PUFA and/or carotenoid are used as a source for biofuel.

In another embodiment, enhancement or enhancing production and/or expression is measured against control cells exposed to the same conditions which do not express OGP according to the present invention. In another embodiment, enhancement or enhancing production and/or expression of cells transfected or transduced with OGP is measured against control cells exposed to the same conditions.

In another embodiment, the method for increasing oil globules and/or carotenoid such as astaxanthin content in a cell comprises the step of over expressing a polynucleotide sequence encoding a self (endogenous) OGP in a cell. In another embodiment, the method for increasing oil, PUFA, oil globules and/or carotenoid content in a microalga cell comprises the step of over expressing a polynucleotide sequence encoding a self OGP in a microalga cell. In another embodiment, the method for increasing oil, PUFA, oil globules and/or astaxanthin content in *H. pluvialis* comprises the step of over expressing a polynucleotide sequence encoding *H. pluvialis* OGP in *H. pluvialis*. In another embodiment, the method for increasing oil, PUFA, oil globules and/or astaxanthin in *H. pluvialis* comprises the step of over expressing the polynucleotide sequence of SEQ ID NO: 2 or SEQ ID NO: 3 in *H. pluvialis*.

In another embodiment, the method for increasing oil, PUFA, oil globules and/or carotenoid content in a cell further comprises the step of subjecting the cell or a freshwater alga such as *H. pluvialis* to a condition selected from: high (intense) light, high salinity, low nutrients, or any combination thereof. In another embodiment, the method for increasing or de-novo producing an oil globule and/or astaxanthin content in a cell further comprises the step of subjecting the cell or a freshwater alga such as *H. pluvialis* to temperate conditions.

In another embodiment, algae as described herein are eukaryotic organisms. In another embodiment, algae as described herein are photoautotrophic. In another embodiment, algae as described herein are mixotrophic. In another embodiment, algae as described herein are unicellular. In another embodiment, algae as described herein are multicellular. In another embodiment, algae as described herein are Excavata algae. In another embodiment, algae as described herein are Rhizaria algae. In another embodiment, algae as described herein are Chromista algae. In another embodiment, algae as described herein are Alveolata algae.

In another embodiment, algae as described herein are Chlorophyta. In another embodiment, algae as described herein are Haematococcaceae. In another embodiment, alga is a freshwater alga or microalga. In another embodiment, algae as described herein produce astaxanthin.

In another embodiment, transforming a first alga with an algal gene derived from a second alga results in enhanced production of oil globules. In another embodiment, transforming a first alga with an algal gene derived from a second alga results in enhanced or de-novo production of oil globules comprising astaxanthin. In another embodiment, transforming an alga with an algal gene derived from the same alga such as described herein results in enhanced production of oil globules. In another embodiment, transforming an alga with an algal gene derived from the same alga such as described herein results in increased production of astaxanthin. In another embodiment, transforming an alga with an algal gene derived from the same alga such as described herein, under the control of a constitutively active promoter, results in enhanced production of oil globules.

In another embodiment, enhanced production of oil globules is enhanced number of oil globules per cell. In another embodiment, enhanced production of oil globules is enhanced astaxanthin content per cell and/or per oil globule.

In another embodiment, transformation and inducement of OGP expression results in enhanced biosynthesis of oil globules and/or astaxanthin. In another embodiment, transformation and inducement via an inducible promoter or a constitutively active promoter results in enhanced biosynthesis of oil globules and/or astaxanthin. In another embodiment, transformation and inducement via an inducible promoter or a constitutively active promoter controlling OGP results in enhanced biosynthesis of oil globules and/or astaxanthin. In another embodiment, transformation and inducement via an inducible promoter or a constitutively active promoter controlling an OGP results in increase in the number of oil globules.

In another embodiment, a DNA sequence as described herein is used to engineer a transgenic organism. In another embodiment, the DNA sequences comprise the sequences provided in SEQ ID NOs: 2 and 3 or variants of these sequences due, for example, to base substitutions, deletions, and/or additions.

In another embodiment, the present invention provides an expression vector comprising the polynucleotide as described herein. In another embodiment, the present invention provides a combination of expression vectors each comprising a polynucleotide as described herein. In another embodiment, the present invention provides a plant specific expression vector comprising the polynucleotide as described herein. In another embodiment, the present invention provides an algal specific expression vector comprising the polynucleotide as described herein. In another embodiment, the present invention provides a cell comprising the expression vector/s as described herein. In another embodiment, the expression vector/s is contained within an *agrobacterium*. In another embodiment, a cell is a bacterial cell, an animal cell, plant cell or an algal cell.

In another embodiment, the present invention provides a transformed bacterium, a transgenic plant, a transgenic seed, or a transgenic alga transformed by a polynucleotide as described herein. In another embodiment, the present invention provides a transformed bacterium, a transgenic plant, a transgenic seed, or a transgenic alga transformed by any combination of polynucleotides as described herein. In another embodiment, the present invention provides that the transgenic plant is true-breeding for the polynucleotide/s as described herein. In another embodiment, the present invention provides a transgenic seed, produced by a transgenic plant transformed by the polynucleotide/s as described herein. In another embodiment, transformed bacteria, a transformed cell, a transgenic plant, a transgenic seed, or a transgenic alga as described herein produces of oil globules and/or astaxanthin.

In another embodiment, expression of the protein's of the invention in plants or seed requires subcloning an ORF/s sequence encoding the protein/s into a plant expression vector, which may comprise a viral 35S promoter, and a Nos terminator. In another embodiment, a cassette or promoter/coding sequence/terminator is then be subcloned into the plant binary transformation vector, and the resulting plasmid introduced into *Agrobacterium*. In another embodiment, the *Agrobacterium* strain transforms the plant. In another embodiment, the *Agrobacterium* strain transforms the plant by the vacuum-infiltration of inflorescences, and the seeds harvested and plated onto selective media containing an antibiotic. In another embodiment, the plasmid confers resistance to an antibiotic, thus only transformed plant material will grow in the presence of an antibiotic. In another embodiment, resistant lines are identified and self-fertilized to produce homozygous material. In another embodiment, leaf material is analyzed for expression of the protein comprising ST activity. In another embodiment, leaf material is analyzed for expression of a combination of protein comprising ST activity. In another embodiment, transformation of an OGP as described herein is a nuclear transformation. In another embodiment, transformation of an OGP as described herein is organellar transformation. In another embodiment, transformation of an OGP as described herein is a chloroplast transformation. In another embodiment, transformation of an OGP as described herein is a mitochondrial transformation.

In another embodiment, the present invention provides that the methods as described herein can be utilized for the de-novo production of oil globules and/or astaxanthin in a cell. In another embodiment, the present invention provides that the methods as described herein can be utilized for the production of oil globules and/or astaxanthin in cells or organisms that do not produce astaxanthin endogenically (in the wild-type). In another embodiment, the present invention provides that the methods as described herein can be utilized for production of astaxanthin in plant cells or a plant.

In another embodiment, the present invention provides that transforming a cell or an organism, transfecting a cell or creating a transgenic organism in accordance to the methods of the invention results in an enhanced production of oil globules and/or astaxanthin in cells that produce oil globules and/or astaxanthin naturally. In another embodiment, the present invention provides that transforming a cell or an organism, transfecting a cell, or creating a transgenic organism in accordance with the invention results in an enhanced production of oil globules and/or astaxanthin in cells that do not produce astaxanthin naturally. In another embodiment, the present invention provides that transforming a cell or an organism, transfecting a cell, or creating a transgenic organism in accordance to the invention results in increased or enhanced production of oil globules and/or astaxanthin that were produced in a lesser quantity prior to transformation or transfection with a DNA molecule comprising a coding region encoding OGP.

In another embodiment, the terms "enhanced production of oil globules and/or astaxanthin", "over expression of OGP", "increased production of oil globules and/or astaxanthin", and "induced production of oil globules and/or astaxanthin", are used interchangeably.

In another embodiment, the level of expression of OGP correlates with the amount of astaxanthin in a cell. In another embodiment, the level of expression of OGP correlates with the amount of astaxanthin in a cell subjected to conditions that favor the production of astaxanthin as described herein. In another embodiment, an enhanced production of oil globules in a cell correlates with enhanced astaxanthin content in the cell. In another embodiment, an enhanced production of oil globules in a cell correlates with enhanced oil content in the cell. In another embodiment, an enhanced production of oil globules in a cell is the result of the introduction of a vector comprising a DNA molecule as described herein into a cell. In another embodiment, enhanced production of oil globules in a cell is the result of the introduction of a vector comprising a DNA molecule as described herein under the control of a promoter as described herein into a cell. In another embodiment, enhanced production of oil globules in a cell is the result of the introduction of a vector comprising a DNA molecule as described herein under the control of a promoter as described herein into a cell as described herein.

In another embodiment, enhanced expression of OGP in a cell or an organism results in enhanced production of oil globules, oil content, fatty acids content, and/or astaxanthin content compared to the number oil globules, oil content, fatty acids content, and/or astaxanthin present in a cell or an organism prior to the introduction of a DNA molecule as described herein.

In another embodiment, enhanced expression of OGP as described herein results in 5% increase in the number of oil globules, oil content, fatty acids content, and/or astaxanthin content present in a cell. In another embodiment, enhanced expression of OGP as described herein results in 3-10% increase in the number of oil globules, oil content, fatty acids content, and/or astaxanthin content present in a cell. In another embodiment, expression of OGP as described herein results in 7-20% increase in the number of oil globules, oil content, fatty acids content, and/or astaxanthin content present in a cell. In another embodiment, enhanced expression of OGP as described herein results in 10-30% increase in the number of oil globules, oil content, fatty acids content, and/or astaxanthin content present in a cell. In another embodiment, enhanced expression of OGP as described herein results in 10-80% increase in the number of oil globules, oil content, fatty acids content, and/or astaxanthin content present in a cell. In another embodiment, enhanced expression of OGP as described herein results in 10-100% increase in the number oil globules, oil content, fatty acids content, and/or astaxanthin content present in a cell. In another embodiment, enhanced expression of OGP as described herein results in 5-150% increase in the number of oil globules, oil content, fatty acids content, and/or astaxanthin content present in a cell. In another embodiment, enhanced expression of OGP as described herein results in 5-500% increase in the number of oil globules, oil content, fatty acids content, and/or astaxanthin content present in a cell. In another embodiment, enhanced expression of OGP as described herein results in 10-50% increase in the number of oil globules, oil content, fatty acids content, and/or astaxanthin content present in a cell. In another embodiment, enhanced expression of OGP as described herein results in 10-80% increase in the number of oil globules, oil content, fatty acids content, and/or astaxanthin content present in a cell. In another embodiment, enhanced expression of OGP as described herein results in 30-70% increase in the number of oil globules, oil content, fatty acids content, and/or astaxanthin content present in a cell. In another embodiment, enhanced expression of OGP as described herein results in 20-40% increase in the number of oil globules, oil content, fatty acids content, and/or astaxanthin content present in a cell. In another embodiment, enhanced expression of OGP as described herein results in 30-50% increase in the number of oil globules, oil content, fatty acids content, and/or astaxanthin content present in a cell. In another embodiment, enhanced expression of OGP as described herein results in 30-40% increase in the number of oil globules, oil content, fatty acids content, and/or astaxanthin content present in a cell.

In another embodiment, provided herein an OGP gene encoded by the nucleus (and not the chloroplast). In another embodiment, provided herein an OGP gene which encodes a membrane bound protein. In another embodiment, provided herein an OGP gene which encodes an oil globule protein. In another embodiment, provided herein an OGP gene from *H. pluvialis* expressed in *Escherichia coli*. In another embodiment, provided herein an OGP gene from *H. pluvialis* expressed from a prokaryotic expression vector. In another embodiment, provided herein an OGP gene from *H. pluvialis* expressed from a eukaryotic expression vector. In another embodiment, provided herein an OGP gene from *H. pluvialis* expressed from a pET32a prokaryotic expression vector.

In another embodiment, provided herein that the conditions for enhanced oil globule and/or astaxanthin production comprise application of environmental conditions such as but not limited to: light intensity (for example, intense light in the range of about 150-1500 μmol photon $m^{-2}s^{-1}$, and sub ranges thereof), phosphate starvation and salt stress (NaCl 0.8%). In another embodiment, provided herein that the conditions for enhanced oil globule and/or astaxanthin production comprise conditions wherein cell growth is retarded. In another embodiment, cell growth is retarded as reflected by a decrease in cell division rate. In another embodiment, provided herein that the conditions for enhanced oil globule and/or astaxanthin production require a nitrogen source. In another embodiment, provided herein that the conditions for enhanced oil globule and/or astaxanthin production require a change in the cell stage from biflagellate vegetative green cells to non-motile and large resting cells. In another embodiment, provided herein that environmental and/or nutritional stresses, which interfere with cell division, trigger the accumulation of oil globules and/or astaxanthin. In another embodiment, provided herein that the conditions for enhanced oil globule and/or astaxanthin production comprise contacting the algal cells with an inhibitor of cell division. In another embodiment, provided herein that the conditions for enhanced oil globule and/or astaxanthin production comprise contacting the algal cells with a specific inhibitor of cell division was applied, a massive accumulation of astaxanthin occurred. In another embodiment, oil globule and/or astaxanthin content is measured both in weight (mg/g) and in cellular (pg/cell) contents.

In another embodiment, provided herein that the conditions for enhanced oil globule and/or astaxanthin production comprise a high dose of light (intense light). In another embodiment, provided herein that the conditions for enhanced oil globule and/or astaxanthin production comprise a high dose of irradiation. In another embodiment, provided herein that the conditions for enhanced oil globule and/or astaxanthin production comprise a combination of nitrogen deficiency and a salt or an ester of an acid such as acetate addition.

In another embodiment, oil globule and astaxanthin accumulation is induced by growing a cell culture expressing OGP endogenically or exogenically in nitrate-free mBG-11 medium. In another embodiment, oil globule and astaxanthin accumulation is induced by growing a cell culture expressing OGP endogenically or exogenically by subjecting the cells to intense light of, for example, 330-380 µmol photon $m^{-2}s^{-1}$ (high light, HL). In some embodiments, intense light is sunlight. In another embodiment, oil globule is present in a cell wall.

Figure 2:
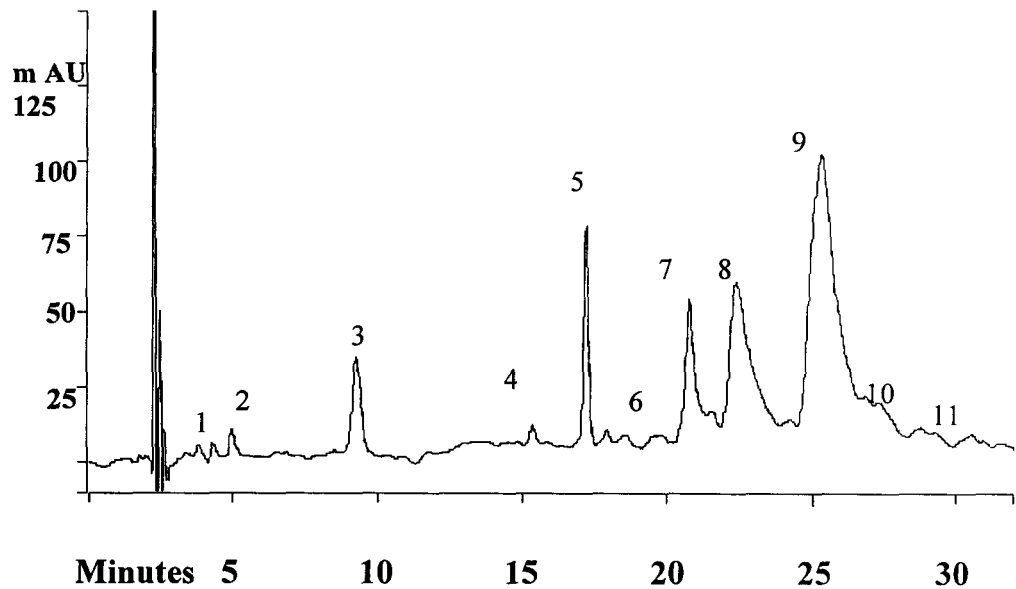
FIG. 2: HPLC chromatogram of the pigment extract from *H. pluvialis* oil globules. Peaks: 1, antheraxanthin; 2, lutein; 3, zeaxanthin; 4, astaxanthin ester 1; 5, chlorophyll b; 6, astaxanthin ester 2; 7, chlorophyll a+astaxanthin ester 3; 8-11, Astaxanthin esters 5, 6, 7, and 8.
Figure 3:
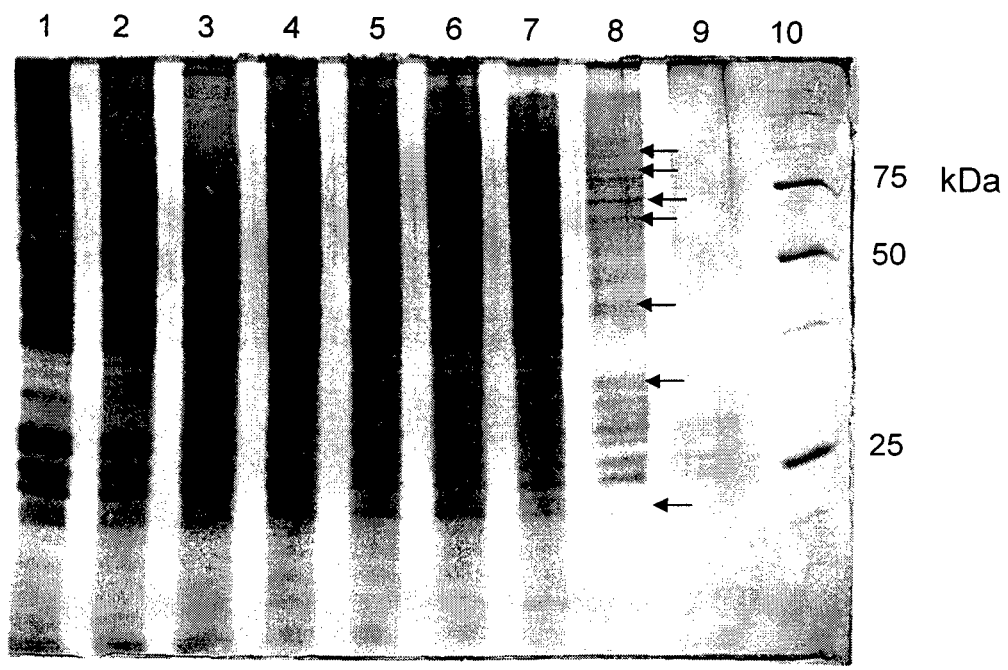
FIG. 3: Depicts micrographs of SDS-PAGE of *H. pluvialis*: 1-7 total homogenate during stress induction of days 0, 2, 4, 6, 8, 10, 12; 8, oil globules; 9, microsomes; 10, marker. At day 0 cells are green (astaxanthin and oil free) while in all other days cells are red cells (astaxanthin and oil rich) Arrows indicate the proteins suspected to be globule associated.
Figure 5:
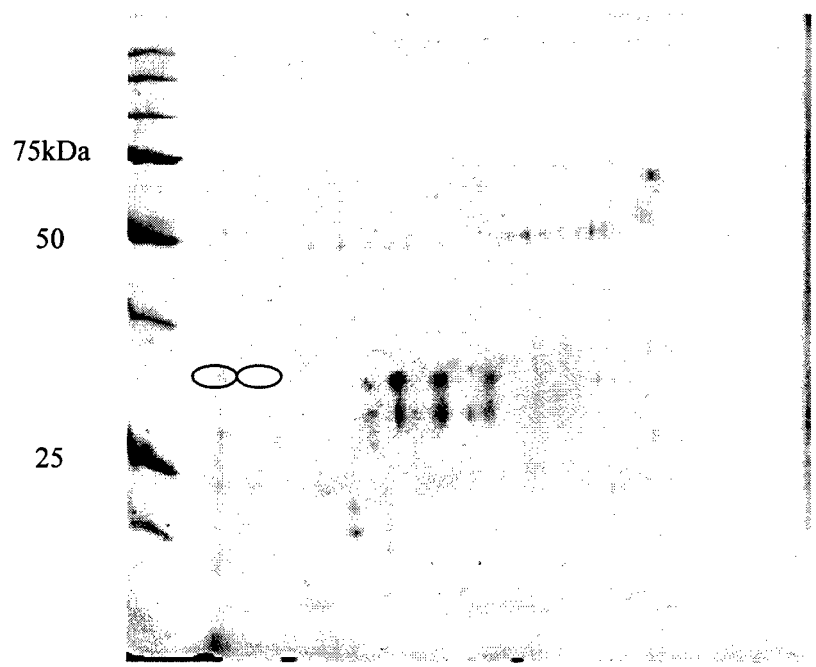
FIG. 5: Depicts micrographs of 2D gel of *H. pluvialis* globules protein. The marked bands were excised and taken for MS analysis.

In another embodiment, oil globules are isolated by washing in ionic strength, chaotropic agent and detergent wash. In another embodiment, astaxanthin in an oil globule is astaxanthin ester. In another embodiment, astaxanthin is astaxanthin ester. In another embodiment, oil globules comprise chlorophyll and the chloroplast oriented xanthophylls: antheraxanthin, lutein and zeaxanthin (FIG. 2). In another embodiment, oil globules comprise four major fatty acids: 16:0, 18:1, 18:2 and 18:3ω3. In another embodiment, oil globules comprise a protein band having a relative MW of ~20-30 kDa (FIG. 3 lane 8). In another embodiment, oil globules comprise a protein band having a relative MW of 33 kD designated oil globule protein (OGP) (FIG. 5).

In another embodiment, an engineered organism is engineered to express OGP as described herein. In another embodiment, an engineered organism is engineered to highly express OGP as described herein. In another embodiment, an engineered plant or alga as described herein is used for the manufacturing astaxanthin. In another embodiment, an engineered plant as described herein is used for manufacturing desired fatty acids.

In some embodiments, "protein", "OGP", or "polypeptide" as used herein encompasses native polypeptides (either degradation products, synthetically synthesized polypeptides or recombinant polypeptides) and peptidomimetics (typically, synthetically synthesized polypeptides), as well as peptoids and semipeptoids which are polypeptide analogs, which have, in some embodiments, modifications rendering the polypeptides/proteins even more stable while in-vivo or more capable of penetrating into cells.

In some embodiments, modifications include, but are not limited to N terminus modification, C terminus modification, polypeptide bond modification, including, but not limited to, CH2-NH, CH2-S, CH2-S=O, O=C—NH, CH2-O, CH2-CH2, S=C—NH, CH=CH or CF=CH, backbone modifications, and residue modification. Methods for preparing peptidomimetic compounds are well known in the art and are specified, for example, in Quantitative Drug Design, C. A. Ramsden Gd., Chapter 17.2, F. Choplin Pergamon Press (1992), which is incorporated by reference as if fully set forth herein. Further details in this respect are provided hereinbelow.

In some embodiments, polypeptide bonds (—CO—NH—) within the polypeptide are substituted. In some embodiments, the polypeptide bonds are substituted by N-methylated bonds (—N(CH3)-CO—). In some embodiments, the polypeptide bonds are substituted by ester bonds (—C(R)H—C—O—O—C(R)—N—). In some embodiments, the polypeptide bonds are substituted by ketomethylene bonds (—CO—CH2-). In some embodiments, the polypeptide bonds are substituted by α-aza bonds (—NH—N(R)—CO—), wherein R is any alkyl, e.g., methyl, carbo bonds (—CH2-NH—). In some embodiments, the polypeptide bonds are substituted by hydroxyethylene bonds (—CH(OH)—CH2-). In some embodiments, the polypeptide bonds are substituted by thioamide bonds (—CS—NH—). In some embodiments, the polypeptide bonds are substituted by olefinic double bonds (—CH=CH—). In some embodiments, the polypeptide bonds are substituted by retro amide bonds (—NH—CO—). In some embodiments, the polypeptide bonds are substituted by polypeptide derivatives (—N(R)—CH2—CO—), wherein R is the "normal" side chain, naturally presented on the carbon atom. In some embodiments, these modifications occur at any of the bonds along the polypeptide chain and even at several (2-3 bonds) at the same time.

In some embodiments, natural aromatic amino acids of the polypeptide such as Trp, Tyr and Phe, be substituted for synthetic non-natural acid such as Phenylglycine, TIC, naphthylelanine (Nol), ring-methylated derivatives of Phe, halogenated derivatives of Phe or o-methyl-Tyr. In some embodiments, the polypeptides of the present invention include one or more modified amino acid or one or more non-amino acid monomers (e.g., fatty acid, complex carbohydrates, etc.).

In one embodiment, "amino acid" or "amino acids" is understood to include the 20 naturally occurring amino acids; those amino acid often modified post-translationally in vivo, including, for example, hydroxyproline, phosphoserine and phosphothreonine; and other unusual amino acid including, but not limited to, 2-aminoadipic acid, hydroxylysine, isodesmosine, nor-valine, nor-leucine and ornithine. In one embodiment, "amino acid" includes both D- and L-amino acid.

In some embodiments, the polypeptides or proteins of the present invention are utilized in a soluble form. In some embodiments, the polypeptides or proteins of the present invention include one or more non-natural or natural polar amino acid, including but not limited to serine and threonine which are capable of increasing polypeptide or protein solubility due to their hydroxyl-containing side chain.

In some embodiments, the polypeptides or proteins of the present invention are utilized in a linear form, although it will be appreciated by one skilled in the art that in cases where cyclization does not severely interfere with polypeptide characteristics, cyclic forms of the polypeptide can also be utilized.

In some embodiments, the polypeptides or proteins of the present invention are biochemically synthesized such as by using standard solid phase techniques. In some embodiments, these biochemical methods include exclusive solid phase synthesis, partial solid phase synthesis, fragment condensation, or classical solution synthesis. In some embodiments, these methods are used when the polypeptide is relatively short (about 5-15 kDa) and/or when it cannot be produced by recombinant techniques (i.e., not encoded by a nucleic acid sequence) and therefore involves different chemistry.

In some embodiments, solid phase polypeptide or protein synthesis procedures are well known to one skilled in the art and further described by John Morrow Stewart and Janis Dillaha Young, Solid Phase Polypeptide Syntheses (2nd Ed., Pierce Chemical Company, 1984). In some embodiments, synthetic polypeptides or proteins are purified by preparative high performance liquid chromatography [Creighton T. (1983) Proteins, structures and molecular principles. WH Freeman and Co. N.Y.], and the composition of which can be confirmed via amino acid sequencing by methods known to one skilled in the art.

In some embodiments, recombinant protein techniques are used to generate the polypeptides of the present invention. In some embodiments, recombinant protein techniques are used for generation of relatively long polypeptides (e.g., longer than 18-25 amino acid). In some embodiments, recombinant protein techniques are used for the generation of large amounts of the polypeptide of the present invention. In some embodiments, recombinant techniques are described by Bitter et al., (1987) Methods in Enzymol. 153:516-544, Studier et al. (1990) Methods in Enzymol. 185:60-89, Brisson et al. (1984) Nature 310:511-514, Takamatsu et al. (1987) EMBO J. 6:307-311, Coruzzi et al. (1984) EMBO J. 3:1671-1680 and Brogli et al, (1984) Science 224:838-843, Gurley et al. (1986) Mol. Cell. Biol. 6:559-565 and Weissbach & Weissbach, 1988, Methods for Plant Molecular Biology, Academic Press, NY, Section VIII, pp 421-463.

In one embodiment, a polypeptide or protein of the present invention is synthesized using a polynucleotide encoding a polypeptide or protein of the present invention as described herein. In some embodiments, the polynucleotide encoding a polypeptide of the present invention is ligated into an expression vector, comprising a transcriptional control of a cis-regulatory sequence (e.g., promoter sequence). In some embodiments, the cis-regulatory sequence is suitable for directing constitutive expression of the polypeptide of the present invention. In some embodiments, the cis-regulatory sequence is suitable for directing tissue specific expression of the polypeptide of the present invention. In some embodiments, the cis-regulatory sequence is suitable for directing inducible expression of the polypeptide of the present invention. In another embodiment, a polypeptide is a protein comprising a ST activity as described herein.

In another embodiment, the polynucleotide comprises a genomic polynucleotide sequence. In another embodiment, the polynucleotide comprises a composite polynucleotide sequence.

In one embodiment, the phrase "a polynucleotide" refers to a single or double stranded nucleic acid sequence which be isolated and provided in the form of an RNA sequence, a complementary deoxyribonucleotide sequence (cDNA), a genomic polynucleotide sequence and/or a composite polynucleotide sequences (e.g., a combination of the above).

In one embodiment, "genomic polynucleotide sequence" refers to a sequence derived (isolated) from a chromosome and thus it represents a contiguous portion of a chromosome.

In one embodiment, "composite polynucleotide sequence" refers to a DNA sequence, which is at least partially complementary and at least partially genomic. In one embodiment, a composite sequence can include some exonal sequences required to encode the polypeptide of the present invention, as well as some intronic sequences interposing there between. In one embodiment, the intronic sequences can be of any source, including of other genes, and typically will include conserved splicing signal sequences. In one embodiment, intronic sequences include cis acting expression regulatory elements.

In one embodiment, the polynucleotides of the present invention further comprise a signal sequence encoding a signal peptide for the secretion of the polypeptides of the present invention. In one embodiment, following expression, the signal peptides are cleaved from the precursor proteins resulting in the mature proteins.

In some embodiments, polynucleotides of the present invention are prepared using PCR techniques or any other method or procedure known to one skilled in the art. In some embodiments, the procedure involves the legation of two different DNA sequences (See, for example, "Current Protocols in Molecular Biology", eds. Ausubel et al., John Wiley & Sons, 1992).

In one embodiment, polynucleotides of the present invention are inserted into expression vectors (i.e., a nucleic acid construct) to enable expression of the recombinant polypeptide. In one embodiment, the expression vector of the present invention includes additional sequences which render this vector suitable for replication and integration in prokaryotes. In one embodiment, the expression vector of the present invention includes additional sequences which render this vector suitable for replication and integration in eukaryotes. In one embodiment, the expression vector of the present invention includes a shuttle vector which renders this vector suitable for replication and integration in both prokaryotes and eukaryotes. In some embodiments, cloning vectors comprise transcription and translation initiation sequences (e.g., promoters, enhancers) and transcription and translation terminators (e.g., polyadenylation signals).

In one embodiment, a variety of prokaryotic or eukaryotic cells can be used as host-expression systems to express the polypeptides of the present invention. In some embodiments, these include, but are not limited to, microorganisms, such as bacteria transformed with a recombinant bacteriophage DNA, plasmid DNA or cosmid DNA expression vector containing the polypeptide coding sequence; yeast transformed with recombinant yeast expression vectors containing the polypeptide coding sequence; plant cell systems infected with recombinant virus expression vectors (e.g., cauliflower mosaic virus, CaMV; tobacco mosaic virus, TMV) or transformed with recombinant plasmid expression vectors, such as Ti plasmid, containing the polypeptide coding sequence.

In some embodiments, non-bacterial expression systems are used (e.g., plant expression systems) to express the polypeptide of the present invention.

In one embodiment, yeast expression systems are used. In one embodiment, algae expression systems are used. In one embodiment, plant expression systems are used. In one embodiment, a number of vectors containing constitutive or inducible promoters can be used in yeast as disclosed in U.S.

Pat. No. 5,932,447. In another embodiment, vectors which promote integration of foreign DNA sequences into the yeast chromosome are used.

In another embodiment, expression in a host cell can be accomplished in a transient or a stable fashion. In another embodiment, a host cell is a cell as described herein. In another embodiment, transient expression is from introduced constructs which contain expression signals functional in the host cell, but which constructs do not replicate and rarely integrate in the host cell, or where the host cell is not proliferating. In another embodiment, transient expression also can be accomplished by inducing the activity of a regulatable promoter operably linked to the gene of interest.

In another embodiment, stable expression is achieved by introduction of a construct that integrates into the host genome. In another embodiment, stable expression comprises autonomously replication within the host cell. In another embodiment, stable expression of the polynucleotide of the invention is selected for through the use of a selectable marker located on or transfected with the expression construct, followed by selection for cells expressing the marker. In another embodiment, stable expression results from integration, the site of the construct's integration can occur randomly within the host genome or can be targeted through the use constructs containing regions of homology with the host genome sufficient to target recombination with the host locus. In another embodiment, constructs are targeted to an endogenous locus, all or some of the transcriptional and translational regulatory regions can be provided by the endogenous locus.

In another embodiment, an expression of a protein as described herein comprising OGP activity includes functional transcriptional and translational initiation and termination regions that are operably linked to the DNA encoding the protein comprising an OGP activity. In another embodiment, an expression of proteins as described herein comprising various OGP activities includes functional transcriptional and translational initiation and termination regions that are operably linked to the DNA encoding the proteins comprising OGP activity. In another embodiment, an expression of proteins as described herein comprising OGP activity includes functional transcriptional and translational initiation and termination regions that are operably linked to the DNA encoding the protein comprising a OGP activity. In another embodiment, transcriptional and translational initiation and termination regions are derived from a variety of nonexclusive sources, including the DNA to be expressed, genes known or suspected to be capable of expression in the desired system, expression vectors, chemical synthesis, or from an endogenous locus in a host cell. In another embodiment, expression in a plant tissue and/or plant part presents certain efficiencies, particularly where the tissue or part is one which is harvested early, such as seed, leaves, fruits, flowers, roots, etc. In another embodiment, expression can be targeted to that location in a plant by utilizing specific regulatory sequences that are known to one of skill in the art. In another embodiment, the expressed protein is an enzyme which produces a product which may be incorporated, either directly or upon further modifications, into a fluid fraction from the host plant. In another embodiment, expression of a protein of the invention, or antisense thereof, alters the levels of specific PUFAs, or derivatives thereof, found in plant parts and/or plant tissues. The OGP coding region, in some embodiments, may be expressed either by itself or with other genes, in order to produce cells, tissues, algae, and/or plant parts containing higher proportions of desired oil globules and/or oil globule content. In another embodiment, the OGP coding region, in some embodiments, may be expressed either by itself or with other genes, in order to produce cells, tissues, algae, and/or plant parts containing higher proportions of astaxanthin In another embodiment, the termination region is derived from the 3' region of the gene from which the initiation region was obtained from or from a different gene. In another embodiment, the termination region usually is selected as a matter of convenience rather than because of any particular property.

In another embodiment, a plant or plant tissue is utilized as a host or host cell, respectively, for expression of the protein of the invention which may, in turn, be utilized in the production of polyunsaturated fatty acids. In another embodiment, desired oil or fatty acids of an oil globule are produced in a seed. In another embodiment, methods of isolating seed oils are known in the art. In another embodiment, seed oil components are manipulated through the expression of the protein of the invention in order to provide seed oils that can be added to nutritional compositions, pharmaceutical compositions, animal feeds and cosmetics. In another embodiment, a vector which comprises a DNA sequence encoding the protein as described herein is linked to a promoter, and is introduced into the plant tissue or plant for a time and under conditions sufficient for expression of the protein.

In another embodiment, a vector as described herein comprises additional genes that encode other enzymes, involved in oil globule synthesis and/or modification. In another embodiment, the bacteria, plant tissue or plant produces the relevant substrate upon which the enzymes act or a vector encoding enzymes which produce such substrates may be introduced into the plant tissue, plant cell or plant. In another embodiment, a substrate is in contact with the bacteria, or is sprayed on plant tissues expressing the appropriate enzymes. In another embodiment, the invention is directed to a transgenic plant comprising the above-described vector, wherein expression of the nucleotide sequence of the vector results in production of a polyunsaturated fatty acid in, for example, the seeds of the transgenic plant.

In another embodiment, the regeneration, development, and cultivation of plants from single plant protoplast transformants or from various transformed explants is well known in the art (for example: Weissbach and Weissbach, In: Methods for Plant Molecular Biology, (Eds.), Academic Press, Inc. San Diego, Calif., (1988)). In another embodiment, regeneration and growth process comprises the steps of selection of transformed cells, culturing those individualized cells through the usual stages of embryonic development through the rooted plantlet stage. In another embodiment, transgenic embryos and seeds are similarly regenerated. In another embodiment, resulting transgenic rooted shoots are thereafter planted in an appropriate plant growth medium such as soil. In another embodiment, regeneration and growth process of algae are known to one of skill in the art. In another embodiment, identification, selection, of transgenic algae are known to one of skill in the art.

In another embodiment, development or regeneration of plants containing an exogenous polynucleotide as described herein encodes a protein as described herein and is well known in the art. In another embodiment, development or regeneration of algae containing an exogenous polynucleotide as described herein encodes a protein as described herein and is well known in the art. In another embodiment, the regenerated plants are self-pollinated to provide homozygous transgenic plants. In another embodiment, pollen obtained from the regenerated plants is crossed to seed-grown plants of agronomically important lines. In another embodiment, pollen from plants of these important lines is used to pollinate regenerated plants. In another embodiment, a transgenic plant of the present invention containing a desired polypeptide is cultivated using methods well known to one skilled in the art.

In another embodiment, a variety of methods can be utilized for the regeneration of plants from plant tissue. In another embodiment, the method of regeneration will depend on the starting plant tissue and the particular plant species to be regenerated. In another embodiment, methods for transforming dicots, primarily by use of *Agrobacterium tumefaciens*, and obtaining transgenic plants are known in the art McCabe et al., Biol. Technology 6:923 (1988), Christou et al., Plant Physiol. 87:671-674 (1988)); Cheng et al., Plant Cell Rep. 15:653657 (1996), McKently et al., Plant Cell Rep. 14:699-703 (1995)); Grant et al., Plant Cell Rep. 15:254-258, (1995).

In another embodiment, transformation of monocotyledons using electroporation, particle bombardment, and *Agrobacterium* are known. In another embodiment, transformation and plant regeneration are well established in the art. In another embodiment, assays for gene expression based on the transient expression of cloned nucleic acid constructs have been developed by introducing the nucleic acid molecules into plant cells by polyethylene glycol treatment, electroporation, or particle bombardment (Marcotte et al., Nature 335:454-457 (1988); Marcotte et al., Plant Cell 1:523-532 (1989); McCarty et al., Cell 66:895-905 (1991); Hattori et al., Genes Dev. 6:609-618 (1992); Goff et al., EMBO J. 9:2517-2522 (1990)).

In another embodiment, transient expression systems are used to functionally dissect the oligonucleotides constructs. In another embodiment, practitioners are familiar with the standard resource materials which describe specific conditions and procedures for the construction, manipulation and isolation of macromolecules (e.g., DNA molecules, plasmids, etc.), generation of recombinant organisms and the screening and isolating of clones, (see for example, Sambrook et al., Molecular Cloning: A Laboratory Manual, Cold Spring Harbor Press (1989); Maliga et al., Methods in Plant Molecular Biology, Cold Spring Harbor Press (1995); Birren et al., Genome Analysis: Detecting Genes, 1, Cold Spring Harbor, N.Y. (1998); Birren et al., Genome Analysis: Analyzing DNA, 2, Cold Spring Harbor, N.Y. (1998); Plant Molecular Biology: A Laboratory Manual, eds. Clark, Springer, N.Y. (1997)).

In one embodiment, the expression vector of the present invention can further include additional polynucleotide sequences that allow, for example, the translation of several proteins from a single mRNA such as an internal ribosome entry site (IRES) and sequences for genomic integration of the promoter-chimeric polypeptide.

In some embodiments, expression vectors containing regulatory elements from eukaryotic viruses such as retroviruses are used by the present invention. In some embodiments, recombinant viral vectors are useful for in vivo expression of the polypeptides of the present invention since they offer advantages such as lateral infection and targeting specificity. In one embodiment, lateral infection is inherent in the life cycle of, for example, retrovirus, and is the process by which a single infected cell produces many progeny virions that bud off and infect neighboring cells. In one embodiment, the result is that a large area becomes rapidly infected, most of which was not initially infected by the original viral particles. In one embodiment, viral vectors are produced that are unable to spread laterally. In one embodiment, this characteristic can be useful if the desired purpose is to introduce a specified gene into only a localized number of targeted cells.

In one embodiment, various methods can be used to introduce the expression vector of the present invention into cells. Such methods are generally described in Sambrook et al., Molecular Cloning: A Laboratory Manual, Cold Springs Harbor Laboratory, New York (1989, 1992), in Ausubel et al., Current Protocols in Molecular Biology, John Wiley and Sons, Baltimore, Md. (1989), Chang et al., Somatic Gene Therapy, CRC Press, Ann Arbor, Mich. (1995), Vega et al., Gene Targeting, CRC Press, Ann Arbor Mich. (1995), Vectors: A Survey of Molecular Cloning Vectors and Their Uses, Butterworths, Boston Mass. (1988) and Gilboa et al. [Biotechniques 4 (6): 504-512, 1986] and include, for example, stable or transient transfection, lipofection, electroporation and infection with recombinant viral vectors. In addition, see U.S. Pat. Nos. 5,464,764 and 5,487,992 for positive-negative selection methods.

In one embodiment, plant expression vectors are used. In one embodiment, the expression of a polypeptide coding sequence is driven by a number of promoters. In some embodiments, viral promoters such as the 35S RNA and 19S RNA promoters of CaMV [Brisson et al., Nature 310:511-514 (1984)], or the coat protein promoter to TMV [Takamatsu et al., EMBO J. 6:307-311 (1987)] are used. In another embodiment, plant promoters are used such as, for example, the small subunit of RUBISCO [Coruzzi et al., EMBO J. 3:1671-1680 (1984); and Brogli et al., Science 224:838-843 (1984)] or heat shock promoters, e.g., soybean hsp17.5-E or hsp17.3-B [Gurley et al., Mol. Cell. Biol. 6:559-565 (1986)]. In one embodiment, constructs are introduced into plant cells using Ti plasmid, Ri plasmid, plant viral vectors, direct DNA transformation, microinjection, electroporation and other techniques well known to the skilled artisan. See, for example, Weissbach & Weissbach [Methods for Plant Molecular Biology, Academic Press, NY, Section VIII, pp 421-463 (1988)]. Other expression systems such as insects and mammalian host cell systems, which are well known in the art, can also be used by the present invention.

It will be appreciated that other than containing the necessary elements for the transcription and translation of the inserted coding sequence (encoding the polypeptide or protein), the expression construct of the present invention can also include sequences engineered to optimize stability, production, purification, yield or activity of the expressed polypeptide or protein.

In some embodiments, transformed cells are cultured under effective conditions, which allow for the expression of high amounts of recombinant polypeptide or protein having OGP activity. In some embodiments, effective culture conditions include, but are not limited to, effective media, bioreactor, temperature, pH and oxygen conditions that permit protein production. In one embodiment, an effective medium refers to any medium in which a cell is cultured to produce the recombinant polypeptide or protein of the present invention. In some embodiments, a medium typically includes an aqueous solution having assimilable carbon, nitrogen and phosphate sources, and appropriate salts, minerals, metals and other nutrients, such as vitamins. In some embodiments, cells of the present invention can be cultured in conventional fermentation bioreactors, shake flasks, test tubes, microtiter dishes and petri plates. In some embodiments, culturing is carried out at a temperature, pH and oxygen content appropriate for a recombinant cell. In some embodiments, culturing conditions are within the expertise of one of ordinary skill in the art.

In some embodiments, depending on the vector and host system used for production, resultant polypeptides or proteins of the present invention either remain within the recombinant cell, secreted into the fermentation medium, secreted into a space between two cellular membranes, or retained on the outer surface of a cell or viral membrane.

In one embodiment, following a predetermined time in culture, recovery of the recombinant polypeptide or protein is effected.

In one embodiment, the phrase "recovering the recombinant polypeptide or protein" used herein refers to collecting the whole fermentation medium containing the polypeptide or protein and need not imply additional steps of separation or purification.

In one embodiment, polypeptides or proteins of the present invention are purified using a variety of standard protein purification techniques, such as, but not limited to, affinity chromatography, ion exchange chromatography, filtration, electrophoresis, hydrophobic interaction chromatography, gel filtration chromatography, reverse phase chromatography, concanavalin A chromatography, chromatofocusing and differential solubilization.

In one embodiment, to facilitate recovery, the expressed coding sequence can be engineered to encode the polypeptide or proteins of the present invention and fused cleavable moiety. In one embodiment, a fusion protein can be designed so that the polypeptide or protein can be readily isolated by affinity chromatography; e.g., by immobilization on a column specific for the cleavable moiety. In one embodiment, a cleavage site is engineered between the polypeptide or protein and the cleavable moiety and the polypeptide or protein can be released from the chromatographic column by treatment with an appropriate enzyme or agent that specifically cleaves the fusion protein at this site [e.g., see Booth et al., Immunol. Lett. 19:65-70 (1988); and Gardella et al., J. Biol. Chem. 265:15854-15859 (1990)].

In one embodiment, the polypeptide or protein of the present invention is retrieved in "substantially pure" form.

In one embodiment, the phrase "substantially pure" refers to a purity that allows for the effective use of the protein in the applications described herein.

In one embodiment, the polypeptide or protein of the present invention can also be synthesized using in vitro expression systems. In one embodiment, in vitro synthesis methods are well known in the art and the components of the system are commercially available.

According to some embodiments, the OGP or a portion thereof may be fused to an additional protein to create a chimeric (fusion) protein. In such embodiments, the OGP or a portion thereof may function as a targeting moiety to target said additional protein to an oil globule and as a protecting element, to protect the additional protein from degradation. In some embodiments, the additional protein may be any type of protein. In some embodiments, the additional protein is not a protein which is endogenously expressed within the target cell. In some embodiments, the additional protein is a recombinant protein. In some embodiments, the OGP or a portion thereof is fused to the N' terminal of the additional protein. In some embodiments, the OGP or a portion thereof is fused to the C' terminal of the additional protein. In some embodiments, the OGP or a portion thereof is directly linked to the additional protein, such that the open reading frame (ORF) of the OGP directly precedes the ORF of the additional protein. In some embodiments, the OGP or a portion thereof is directly linked to the additional protein, such that the open reading frame (ORF) of the additional protein directly precedes the ORF of the OGP. In some embodiments, a linker sequence (linker moiety) is located between the ORF's of the OGP and the additional protein. The linker sequence may include, for example, but not limited to a marker, a protease cleavage site, a tag, a flag, an enzyme, and the like that may be further used in the isolation and/or separation of the chimeric protein from a cell lysate expressing the chimeric protein. In some embodiments, the fusion may be expressed from an expression vector constructed by methods well known in the art, such as described hereinabove. In some embodiments, the expression vector may be constructed to include the coding region of the additional protein and the coding region of the OGP or a portion thereof, under the control of a promoter of choose. In some embodiments, the expression vector for the chimeric protein may be expressed in a target cell, whereby upon expression of the chimeric protein within the cell, it will targeted to an oil globule. Targeting of the additional protein to the oil globule may protect the additional protein from degradation within the cell and may be further used for the isolation/separation of said additional protein from a cell extract expressing the fusion protein, for example, by floating centrifuge of the cell extract.

According to some embodiments, there is thus provided a method for separating or isolating an exogenously expressed recombinant protein fused to a OGP or a portion thereof from a target cell, the method comprising introducing an expression vector to the cell, wherein the expression vector comprises the coding sequence of the exogenous recombinant protein linked to the coding sequence of an OGP protein, or to portion thereof, such that both coding sequences are in one reading frame; isolating a fraction comprising oil globules from the cell; and separating or isolating the exogenous recombinant protein from the fraction comprising the oil globules.

In another embodiment, oil globules constituents produced by the methods as described herein are used in the cosmetic industry, the drug industry, food additives industry, baby food industry or any other applicable industry. In another embodiment, oil globules constituents produced by the methods as described herein are used in within a formulation.

In some embodiments, the proteins or oligonucleotides of the invention modified by the covalent attachment of water-soluble polymers such as polyethylene glycol, copolymers of polyethylene glycol and polypropylene glycol, carboxymethyl cellulose, dextran, polyvinyl alcohol, polyvinylpyrrolidone or polyproline. In another embodiment, the modified proteins or oligonucleotides of the invention exhibit substantially longer half-lives in blood following intravenous injection than do the corresponding unmodified compounds. In one embodiment, modifications also increase the proteins or oligonucleotides solubility in aqueous solution, eliminate aggregation, enhance the physical and chemical stability of the compound, and greatly reduce the immunogenicity and reactivity of the compound. In another embodiment, the desired in vivo biological activity is achieved by the administration of such polymer-compound abducts less frequently or in lower doses than with the unmodified compound.

In one embodiment, compositions of the present invention are presented in a pack or dispenser device, such as an FDA approved kit, which contain one or more unit dosage forms containing the active ingredient. In one embodiment, the pack, for example, comprise metal or plastic foil, such as a blister pack. In one embodiment, the pack or dispenser device is accompanied by instructions for administration. In one embodiment, the pack or dispenser is accommodated by a notice associated with the container in a form prescribed by a governmental agency regulating the manufacture, use or sale of pharmaceuticals, which notice is reflective of approval by the agency of the form of the compositions or human or veterinary administration. Such notice, in one embodiment, is labeling approved by the U.S. Food and Drug Administration for prescription drugs or of an approved product insert.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N. Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference. Other general references are provided throughout this document.

Experimental Procedures

Materials and Methods
*Haematococcus pluvialis* Strain
*H. pluvialis* Flotow 1844 em. Wille K-0084 (Chlorophyceae, order Volvocales) was obtained from the Scandinavia Culture Center for Algae and Protozoa (SCCAP) at the University of Copenhagen, Denmark.
Growth Conditions of Algal Cultures
*H. pluvialis* algal culture was cultivated as previously described (Zhekisheva et al., 2005). For the induction of astaxanthin accumulation, cultures were inoculated in nitrate-free mBG-11 medium to a final cell concentration of $2 \times 10^5$ cell·mL$^{-1}$ and subjected to 350 µmol photon m$^{-2}$s$^{-1}$ (high light, HL). After 7 days, red cells were harvested for globule isolation. Contents of chlorophyll and astaxanthin at harvest were 3.9 and 132 µg·mL$^{-1}$ respectively.
RNA Isolation
For RNA isolation axenic cultures were grown in 250 mL flask containing 100 mL of mBG-11 in a shaker (150 RPM, 90 µmol photon m$^2$s$^{-1}$) up to cell concentration of $2 \times 10^5$ cell·mL$^{-1}$. Then cells were transferred to 250 mL flasks containing 50 mL of nitrogen depleted mBG-11 medium and light intensity of 200 µmol photon m$^2$s$^{-1}$ to induce astaxanthin accumulation. For each sample (0, 12, 24, 48 and 72 hour) a separated flask was harvested.
Measurement of Growth Parameters, Extraction and Quantification of Pigments
Culture cell concentration, chlorophyll quantification and total carotenoids quantification were done as previously described (Zhekisheva et al., (2002) J Phycol 38:325-331).
Globules Isolation
*H. pluvialis* culture was harvested by centrifugation (1500 g, 10 min), suspended in breakage buffer 0.2 M sucrose (10 mM MOPS, pH 7.0, 10 mM KCl, 5 mM Na-EDTA, 1 mM DTT, 1 mM PMSF, 1 mM Benzamidine, 0.5 mg/mL Leupeptine) and ruptured with mini beadbeater (Biospec products. OK. USA) using 2.5 mm glass beads for 4 min. The resulting homogenate was centrifuged (1500×g 10 min) and cell-free extract recovered was fractionated by centrifugation (25000 g×60 min, Sorvall RC 5C plus) on discontinuous sucrose flotation gradient (0.6, 0.4, 0.2, 0 M in breakage buffer). The sucrose gradient upper layer containing the oil globules was collected and recentrifuged in ultra centrifuge (100000 g×120 min, Sorvall Combi plus). The oily floating layer was collected in 0.3 mL aliquots and frozen (−20° C.) until it was analyzed.
HPLC Pigment Analysis
In order to determine pigment profile, HPLC analysis was applied as described in Zhekisheva et al (2005). Astaxanthin and chlorophylls were identified according to their standards and astaxanthin isomers were identified by their UV-VIS absorbance spectra, according to Yuan and Chen (1997), Biotechnol Tech 11(7):455-459. Xanthophylls, other than astaxanthin, were identified by their absorbance spectra and calculated peak III/II ratio, according to Briton et al (2004), Carotenoids handbook, Birkhauser, Basel, Switzerland.
Lipid Analysis
Lipids were extracted with diethyl ether and analyzed as described in Zhekisheva et al (2005). C17 was used as internal standard. Samples were analysed by gas chromatography (hp 5890) on a Supelcowax 10 (Supleco Inc., Bellefonte, Pa., USA) fused silica capillary column.
Protein Analysis
Protein samples were prepared as described in Wang et al ((2004), Anal Biochem 329:139-141), and the BCA method was used for protein determination (Smith et al., 1985). Protein separation of isolated fractions was performed by SDS PAGE (12%) according to Laemmli (1970), Nature 227:680-685, with minor changes. Samples were prepared by one hour incubation in sample buffer containing 80 mM DTT at room temperature. Bio Rad Precision Plus protein unstained standards was used as a marker. 2D gel was prepared as described in (Liska et al., (2004), Plant Physiol 136:2806-2817) with minor changes. Samples of 130 µl containing 50 µg protein were loaded on 7-cm IEF dry strips, pH 3 to 10 nonlinear (Amersham Biosciences AB, Uppsala). Protein spots of about 33 kD were selected for analysis by MS.

Partial Amino Acid Sequencing

Protein spots were manually excised from 2-D gels and in-gel digested with trypsin. The peptide mixtures was solid phase extracted with C18 resin filled tip (ZipTip Milipore, Billerica, Mass. USA) and nanosprayed into the Orbi-trap MS system in 50% $CH_3CN$ 1% CHOOH solution. Mass spectrometry was carried out with Orbi-trap (Thermo Finnigen) using nanospray attachment (Wilm and Mann, 1996, Anal Chem 68:1-8). Data analysis was done using bioworks 3.3 package and database searches were performed against the NCBInr database with the Sequest package and with Mascot package (Matrix Science, England). De novo sequencing was done using the Biolynx package (Micromass, England).

Isolation of Total RNA

Isolation was performed by SV Total RNA Isolation kit (Promega USA). 40 ml of $2\times10^5$ cell·mL$^{-1}$ were harvested, resuspended in the kit lysis buffer and broken in mini beadbeater (Biospec products. OK. USA) using 2.5 mm glass beads for 4 min. RNA samples were quantified with Nano Drop (ND-1000, Thermo scientific, USA) spectrophotometer and stored at −80° C.

cDNA Preparation, PCR and Sequencing cDNA was synthesized from total RNA by the Reverse iT 1$^{st}$ Strand Synthesis Kit (ABgene, UK) according to the manufacturer's instructions. PCR amplification using degenerate primers was carried out using touch down PCR 56° C. to 46° C. Full length cDNA was synthesized according to the protocol described in the manufacturer's instructions (BD SMART RACE. Clontech). Sequence analyses were performed with the GenBank using BLAST program (Altschul et al. 1990, J Mol Biol 215:403-410).

TABLE 1

Primers used for cloning and expression of OGP

```
Degenerative
peptide no. 1: NDAWN MCAS (SEQ ID NO: 4)
1FOR: 5' GAY GCN TGG AAY ATG TG 3'
(SEQ ID NO: 5)
1REV: 5' CA CAT RTTCCA NGC RTC 3'
(SEQ ID NO: 6)

peptide no. 2: QVGDPVAV (SEQ ID NO: 7)
2FOR: 5' GTN GGN GAY CCN GTN GC 3'
(SEQ ID NO: 8)
2REV: 5' GC NAC NGG RTC NCC NAC 3'
(SEQ ID NO: 9)

peptide no. 3: TAPVVAQAQDL (SEQ ID NO: 10)
3FOR: 5' CCN GTN GTN GCN CAR GC 3'
(SEQ ID NO: 11)
3REV: 5' GCYTG NGCNACNAC NGG 3'
(SEQ ID NO: 12)

Differential expression
For 5' AGCGGGAGATAGTGCGGGACA 3'
(SEQ ID NO: 13)
Rev 5' ATGCCCACCGCCTCCATGC 3'
(SEQ ID NO: 32)

For 5' CAGCACGCCCTGGACACCCTGAAC 3'
(SEQ ID NO: 14)
Rev 5' GGTTTGGGTGACTGGGTCGGCTGT 3'
(SEQ ID NO: 15)

RACE
GSP3 5' ACAAGGCGGTGGCAGACGGGAAG3'
(SEQ ID NO: 16)
```

TABLE 1-continued

Primers used for cloning and expression of OGP

```
NGSP3 5' CAGCACGCCCTGGACACCCTGAAC3'
(SEQ ID NO: 17)

5 ukII 5' ATCAACTACGCCCTTCTTCCCGTCTG3'
(SEQ ID NO: 18)
5 ukIII 5' AAAGTAGCTGTTGCTCGTGGCGATG3'
(SEQ ID NO: 19)
```

Example 1

Globule Isolation

Oil globule accumulation was induced by resuspending exponentially growing culture (chlorophyll and astaxanthin were 5 and 1 μg·mL$^{-1}$, respectively) in nitrate-free mBG-11 medium to a cell concentration of $2\times10^5$ cell·mL$^{-1}$. Culture was subjected to intense light at 350 μmol photon m$^2$s$^{-1}$ (high light, HL) and after 7 days red cells were harvested for globule isolation. Contents of chlorophyll and astaxanthin at harvest were 3.9 and 132 μg·mL$^{-1}$, respectively.

Figure 1:
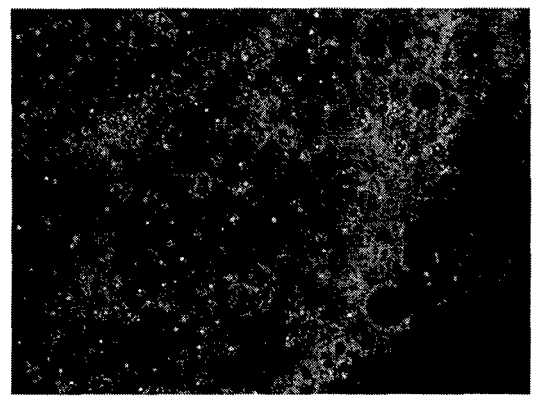
FIG. 1: A micrograph showing *H. pluvialis* isolated oil globules. Bar 20 μm.

The isolation of pure globules from *H. pluvialis* has a huge hurdle in the form of the cell wall. Different methods for cell breakage including grinding, French press or freeze thaw cycles were first examined. In addition different strains which display altered cell wall morphology were tested. Lastly isolated globules were subjected to different purification treatments including washes in ionic strength, chaotropic agent and detergent wash (Tzen, J. T. C. (1997), (Journal of Biochemistry 121, 762-768)). All different procedures produced very similar results regarding the appearance of the isolated globules fraction, the pigments, fatty acids and protein profiles which suggest that purification of contaminating membranes and proteins introduced into globules during cell breakage are very hard or impossible to remove later. Light microscopy show various red vesicles, but also yellow-green ones with diameter ranging from about 200 nm to 4 μM (FIG. 1).

Nevertheless, this highly astaxanthin and oil accumulating strain allowed distinguishing the globule and non globule components by comparing the total cell homogenate profile recovered from broken cells, to that of the isolated floating oil layer.

Example 2

Pigments Analysis

The majority of pigments in isolated globules were astaxanthin esters. Eight different astaxanthin esters comply for about 70% of total pigments in total cell homogenate, while in the isolated globules it increases to about 86% out of total pigments. The major three peaks were astaxanthin esters 3, 5 and 6 (peaks 7, 8 and 9, respectively, in FIG. 2). The later two, were found to be of the trans isomer according to their UV-VIS absorbance spectra (not shown). Except for astaxanthin esters minor amounts of chlorophyll and the chloroplast oriented xanthophylls: antheraxanthin, lutein and zeaxanthin were also detected (FIG. 2). Chlorophylls percentage decrease from 12.7% in total homogenate to 4.5% in the globules (Table. 2). The other three xanthophylls percentage also decreases in the oil globule fraction compared to total homogenate.

TABLE 2

Pigment composition (% of total) of total homogenate or oil globules. Samples containing 10 μg of total pigments were injected to HPLC. Ant—antheraxanthin; Lut—lutein; Zea—zeaxanthin; Ast—astaxanthin ester; Chl—chlorophyll; Rt—retention time

|  | Ant | Lut | Zea | Ast 1 | Chl b | Ast 2 | Chl a |
|---|---|---|---|---|---|---|---|
| Rt (min) | 4.10 | 4.70 | 8.50 | 14.90 | 16.90 | 19.20 | 20.40 |
| Total homogenate | 2.55 | 3.95 | 13.90 | 0.00 | 6.41 | 0.00 | 6.25 |
| Oil globules | 1.49 | 1.69 | 5.77 | 1.91 | 1.88 | 1.06 | 2.65 |

|  | Ast 3 | Ast 4 | Ast 5 | Ast 6 | Ast 7 | Ast 8 |
|---|---|---|---|---|---|---|
| Rt (min) | 20.50 | 20.90 | 22.00 | 24.60 | 26.40 | 27.80 |
| Total homogenate | 7.56 | 1.53 | 17.44 | 36.71 | 2.00 | 1.72 |
| Oil globules | 10.53 | 3.03 | 23.46 | 42.85 | 3.67 | 0.00 |

Example 3

Fatty Acids Analysis

Fatty acid composition of total homogenate and oil globules was very similar, and characterized by the four major fatty acids: 16:0, 18:1, 18:2 and 18:30. These fatty acids represented about 76% and 80% of TFA in total homogenate and oil globules, respectively (Table. 3). It was also shown that in the globules 16:0 is decreasing while 18:1, 18:2 are increasing compared to the total homogenate. The rest were minor fatty acids detected in both samples, including 16:1, 16:2, 16:3, 16:4, 18:0, 18:3 ω6, 18:4, 20:0, 20:1, 20:2, 20:3, 20:4, 22:0.

TABLE 3

Major fatty acid composition (% of total) of total homogenate or oil globules. ± is SD

|  | 16-0 | 18-1 | 18-2 | 18-3ω3 | others |
|---|---|---|---|---|---|
| Total homogenate | 25.69 ± 2.72 | 18.96 ± 0.68 | 21.85 ± 1.15 | 9.69 ± 0.93 | 23.81 |
| Oil globules | 22.36 ± 1.72 | 23 ± 3.19 | 24.92 ± 3.46 | 9.82 ± 1.87 | 19.89 |

Example 4

Proteins Analysis

Figure 4:
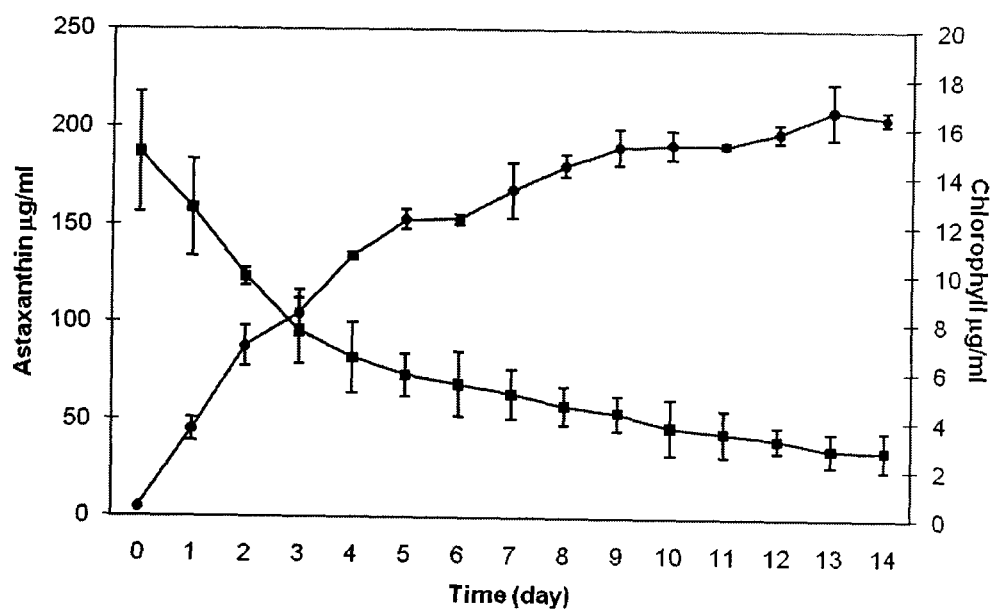
FIG. 4: Is a graph showing the changes in chlorophyll (■, right axis) and astaxanthin (●, left axis) contents during 14 days of oil globule accumulation inductive conditions.

The major protein band of the isolated globules had a relative MW of ~20-30 kDa (FIG. 3 lane 8). However, these bands were highly abundant in total homogenate fraction of both green (astaxanthin and oil free) and red (astaxanthin and oil rich) cells and their quantity decreased over induction period (FIG. 3 lanes 1 and 7). They were thus suspected to be isolation contaminants. Indeed western blots analysis with anti light harvesting complex proteins (LHC) antibodies approved that these are LHC proteins (not shown). To reveal the native proteins of the globules, the changes in protein profile during 14 days of exposure to astaxanthin and oil accumulation inductive conditions, were followed. Culture chlorophyll and astaxanthin are shown in FIG. 4.

During globule accumulation only a few protein bands seem to increase as the total protein decreased. Out of these proteins, 7 different bands were discovered in the globules but not in the microsomal fraction. These proteins are all globule associated proteins (FIG. 3).

Globule proteins were also analyzed on 2D gel. A protein spot of about 33 kD designated oil globule protein (OGP), which was accumulated in correlation with astaxanthin accumulation, found in the globules and is absent from the microsomal fraction was taken for MS analysis (FIG. 5). The peptides sequences detected in OGP MS analysis are shown in Table 4.

TABLE 4

MS produced peptide sequences. Asterisk marks sequences used for degenerate primers design Sequence QVGDPVAV* (SEQ ID NO: 20)
TAPVVAQAQDL* (SEQ ID NO: 21)
TAQSLGTYTL (SEQ ID NO: 22)
TADPVTQTGDDGF* (SEQ ID NO: 23)
NDAWNMCASV* (SEQ ID NO: 24)
MPTFVE (SEQ ID NO: 25)
DTLVSNV (SEQ ID NO: 26)
VVSTLSPT (SEQ ID NO: 27)
QYLATSNQANQD* (SEQ ID NO: 28)
LDLTLSRTTTTFC (SEQ ID NO: 29)
ETSNQQTSAAD (SEQ ID NO: 30)
GVSTLSWATTTT (SEQ ID NO: 31)

Example 5

OGP Gene Analysis

Using degenerate primers designed from MS generated peptides (see M&M), an ORF coding for MS generated peptides, was identified. Further 3 and 5 RACE PCR identified the full length ORF of 825 bp coding for a 275 amino acids protein. Multiple sequence alignment of H. pluvialis OGP protein with putative green algal orthologs reveled identities of 40%, 38% and 36% with Volvox carteri f. Nagariensis (accession no. FD812477), Polytomella parva (accession no. EC748417) and Chlamydomonas reinhardtii (accession no. XP_001697668), respectively (FIG. 6). Significant alignment with 27% identity was also found with Coccomyxa sp (accession number GW230985).

A phylogram estimating evolutionary relationships between these proteins is shown in FIG. 7. To characterize OGP gene, cultures were induced to accumulate astaxanthin (see M&M) for a period of 72 h, during which RNA was isolated at the indicated time intervals (FIG. 8). Accumulation of astaxanthin can be detected in total pigment extract by spectrophotometer already after 12 hours. During the 72 h astaxanthin concentration increased from 2.1 to 26.4 $\mu g \cdot mL^{-1}$ while chlorophyll with minor fluctuations stays leveled. Transcripts levels of OGP gene which were almost undetected in green non stressed cells increased after 12 h of oil globule accumulation inductive conditions by more than 100 fold, stayed leveled up to 48 h and after 72 h were shown to decrease (FIG. 9).

According to the results of the present invention astaxanthin is the only carotenoid accumulated in the globules. Three astaxanthin esters comprise the majority of astaxanthin with absorbance maxima at 476.6-480 nm. Confocal imaging of live cells after the chloroplast was segregated from the oil globules by centrifugation showed no association of chlorophylls with cytoplasmic oil globules (not shown). No free astaxanthin in globules nor n-carotene were detected.

Oil globule tri-acyl-glycerols (TAGs) may serve as an internal buffering system that can rapidly provide specific acyl groups in order to stabilize membranes in a fluctuating environment. Fatty acids content of isolated globules highly resembled that of the total cell homogenate as oil globules TAGs in these cells comprise the majority of lipids (Zhekisheva et al., 2002, J Phycol 38:325-331). Still the present data shows an increase in 18:1 and 18:2 in isolated globules compared to total homogenate indicating that these are the major fatty acids in globule TAG.

The invention claimed is:

1. A plant extract comprising a polynucleotide encoding the amino acid sequence set forth in SEQ ID NO: 1, wherein said polynucleotide is operably linked to a heterologous promoter and wherein said plant extract is obtained from a plant that does not produce astaxanthin endogenically.

2. An expression vector comprising a heterologous promoter operably linked to a polynucleotide encoding the amino acid sequence of SEQ ID NO: 1.

3. A cell comprising the expression vector of claim 2.

4. A transgenic plant, a transgenic seed, a transgenic heterotrophic microorganism, a transformed bacterium, or a transgenic alga comprising a polynucleotide encoding the amino acid sequence set forth in SEQ ID NO: 1.

5. A transgenic seed, produced by a transgenic plant transformed by a polynucleotide encoding the amino acid sequence set forth in SEQ ID NO: 1.

6. A method of enhancing production of oil or oil globules in a cell comprising the step of transforming said cell with a polynucleotide encoding the amino acid sequence set forth in SEQ ID NO: 1, thereby enhancing the production of oil or oil globules in a cell.

7. The method of claim 6, wherein said cell is a plant cell, or an algal cell.

8. A method of enhancing a production of a carotenoid in a cell comprising the step of transforming said cell with a polynucleotide encoding the amino acid sequence set forth in SEQ ID NO: 1, thereby enhancing the production of carotenoid in a cell.

9. The method of claim 8, wherein said cell is a microalgae cell, a plant cell, a heterotrophic microorganism or a yeast cell.

10. The method of claim 8, wherein said carotenoid is astaxanthin.

11. A method of enhancing production of astaxanthin in a *Haematococcus pluvialis* cell comprising the steps of:
    (a) transforming said cell with a composite polynucleotide comprising a polynucleotide encoding the amino acid sequence set forth in SEQ ID NO: 1 under the control of an inducible promoter;
    (b) growing said cell under proliferation promoting conditions;
    (c) depriving said cell of nutrients; and
    (d) subjecting said cell to intense light;
    thereby enhancing a production of astaxanthin in a *Haematococcus pluvialis* cell.

* * * * *

SEQUENCE LISTING

```
<160> NUMBER OF SEQ ID NOS: 36

<210> SEQ ID NO 1
<211> LENGTH: 275
<212> TYPE: PRT
<213> ORGANISM: Haematococcus pluvialis

<400> SEQUENCE: 1

Met Ser Glu Lys Gln Leu Lys Arg Leu Gly Phe Val His Gln Gly Ala
1               5                   10                  15

Ser Tyr Ala Tyr Ser Tyr Thr Gly Thr Ala Glu Lys Leu Tyr Lys Thr
            20                  25                  30

Ala Arg Ser Phe Ala Pro Thr Phe Val Glu Pro Thr Leu Ala Gln Val
        35                  40                  45

Glu Asp Arg Val Val Ala Ile Thr Ala Pro Val Val Ala Gln Ala Gln
    50                  55                  60

Asp Leu Ser Glu Lys Ala Leu His Ile Ala Asp Asp Gln Val Glu Cys
65                  70                  75                  80

Ile Val Asn Thr Thr Asp Lys Ala Val Ala Asp Gly Lys Lys Gly Val
                85                  90                  95

Ile Asp Cys Met Asn Gly Val Lys Glu Met His Glu Lys Asn Met Gln
            100                 105                 110

Thr Tyr Ile Ala Thr Ser Asn Arg Tyr Phe Glu Tyr Ile Lys Gly Met
        115                 120                 125

Ser Glu Trp Ala Lys Asp Lys Met Asn Pro Ile Lys Gly Gly Gln His
    130                 135                 140

Ala Leu Asp Thr Leu Asn Ala Ala Ile Ala Lys Ala Gln Glu Ala Thr
145                 150                 155                 160

Asp Pro Asp Val Ala Ala Lys Met Ala Leu Asp Ala Trp Asn Ser Phe
                165                 170                 175

Ala Ser Val Pro Val Val Ala Lys Val Leu Glu Thr Ala Asp Pro Val
            180                 185                 190

Thr Gln Thr Gly Leu Ser Ser Phe Tyr Lys Leu His Asp Thr Leu Val
        195                 200                 205

Ser Trp Pro Leu Tyr Ser Lys Val Val Ser Thr Gly Val Ser Thr Leu
    210                 215                 220

Ser Trp Ala Thr Thr Met Pro Tyr Lys Leu Gly Ala Gln Tyr Met
225                 230                 235                 240

Tyr Pro Leu Val Gln Pro Val Ala Asp Pro Ala Leu Ala Lys Ile Thr
                245                 250                 255

Asn Ser Lys Val Ile Asn Gly Thr Leu Ser Tyr Trp Lys Pro Thr Ala
            260                 265                 270

Ser Ala Ala
        275

<210> SEQ ID NO 2
<211> LENGTH: 828
<212> TYPE: DNA
<213> ORGANISM: Artificial Sequence
```

<220> FEATURE:
<223> OTHER INFORMATION: Synthetic polynucleotide

<400> SEQUENCE: 2

```
atgtcagaga agcagctgaa gcgcttgggc ttcgtgcatc agggagccag ctatgcatac    60
agctacaccg gcacagccga gaaactgtac aagacagcgc gctccttcgc cccaaccttt   120
gtggaaccca ccttggccca ggttgaggat cgcgttgtgg ccatcacagc cccagtggta   180
gcccaagcgc aagacctcag cgagaaggcg ttacacatcg ccgatgacca ggtggactgc   240
atcctgaaca ccaccgacaa ggcggtggca gacgggaaga agggcgtagt tgattgcatg   300
aacggcgtga aggagatgca cgagaagaac atgcaaacct catcgccac gagcaacagc    360
tactttgagt acatcaaggg catctccgac tgggcaaaag ataagctgaa cccaattaag   420
ggcggccagc acgccctgga caccctgaac gccgcgattg ccaaggctca agaggcaact   480
gaccccgacg tggcagctaa gatggctctg gatgcctgga cagctttgc atccgtgcct   540
gtggtggcca aggtactaga cagccgac ccagtcacgc agaccggcct gtcttccttc      600
tacaagctgc acgacaccct ggtgagctgg cccctgtaca gcaaggtggt gtcgaccggg   660
gtgtccaccc tgagctgggc cacaaccacc acgccctaca agctgggcgc ccagtacatg   720
tacccctgg tgcagcccgt ggctgaccca gcattggcca agatcaccaa cagcaaggtc    780
atcaatggca cgctgtcgta ctggaagcca actgcctcgg cagcttga                828
```

<210> SEQ ID NO 3
<211> LENGTH: 910
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (874)..(874)
<223> OTHER INFORMATION: n is a, c, g, or t
<220> FEATURE:
<221> NAME/KEY: misc_feature
<222> LOCATION: (890)..(890)
<223> OTHER INFORMATION: n is a, c, g, or t

<400> SEQUENCE: 3

```
acacatttat tcagccaaat gtcagagaag cagctgaagc gcttgggctt cgtgcatcag    60
ggagccagct atgcatacag ctacaccggc acagccgaga aactgtacaa gacagcgcgc   120
tccttcgccc caacctttgt ggaacccacc ttggcccagg ttgaggatcg cgttgtggcc   180
atcacagccc cagtggtagc ccaagcgcaa gacctcagcg agaaggcgtt acacatcgcc   240
gatgaccagg tggactgcat cctgaacacc accgacaagg cggtggcaga cgggaagaag   300
ggcgtagttg attgcatgaa cggcgtgaag gagatgcacg agaagaacat gcaaacctac   360
atcgccacga gcaacagcta ctttgagtac atcaagggca tctccgactg gcaaaagat    420
aagctgaacc caattaaggg cggccagcac gccctgggaca cctgaacgc cgcgattgcc   480
aaggctcaag aggcaactga ccccgacgtg gcagctaaga tggctctgga tgcctggaac   540
agctttgcat ccgtgcctgt ggtggccaag gtactagaga cagccgaccc agtcacgcag   600
accggcctgt cttccttcta caagctgcac gacaccctgg tgagctggcc cctgtacagc   660
aaggtggtgt cgaccggggt gtccaccctg agctgggcca acaccaccac gccctacaag   720
ctgggcgccc agtacatgta ccccctggtg cagcccgtgg ctgacccagc attggccaag   780
atcaccaaca gcaaggtcat caatggcacg ctgtcgtact ggaagccaac tgcctcggca   840
```

```
gcttgagctc tggtgccagg acctacccac agcngcaggg atagcagccn catcaggcac    900
agtcacggca                                                            910
```

<210> SEQ ID NO 4
<211> LENGTH: 9
<212> TYPE: PRT
<213> ORGANISM: Artificial Sequence
<220> FEATURE:
<223> OTHER INFORMATION: Synthetic peptide

<400> SEQUENCE: 4

Asn Asp Ala Trp Asn Met Cys Ala Ser
1               5

<210> SEQ ID NO 5
<211> LENGTH: 17
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (6)..(6)
<223> OTHER INFORMATION: n is a, c, g, or t

<400> SEQUENCE: 5

```
gaygcntgga ayatgtg                                                    17
```

<210> SEQ ID NO 6
<211> LENGTH: 17
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (12)..(12)
<223> OTHER INFORMATION: n is a, c, g, or t

<400> SEQUENCE: 6

```
cacatrttcc angcrtc                                                    17
```

<210> SEQ ID NO 7
<211> LENGTH: 8
<212> TYPE: PRT
<213> ORGANISM: Artificial Sequence
<220> FEATURE:
<223> OTHER INFORMATION: Synthetic peptide

<400> SEQUENCE: 7

Gln Val Gly Asp Pro Val Ala Val
1               5

<210> SEQ ID NO 8
<211> LENGTH: 17
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (6)..(6)
<223> OTHER INFORMATION: n is a, c, g, or t -continued

```
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (15)..(15)
<223> OTHER INFORMATION: n is a, c, g, or t

<400> SEQUENCE: 8
gtnggngayc cngtngc                                                  17

<210> SEQ ID NO 9
<211> LENGTH: 17
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (15)..(15)
<223> OTHER INFORMATION: n is a, c, g, or t

<400> SEQUENCE: 9
gcnacnggrt cnccnac                                                  17

<210> SEQ ID NO 10
<211> LENGTH: 11
<212> TYPE: PRT
<213> ORGANISM: Artificial Sequence
<220> FEATURE:
<223> OTHER INFORMATION: Synthetic peptide

<400> SEQUENCE: 10

Thr Ala Pro Val Val Ala Gln Ala Gln Asp Leu
1               5                   10

<210> SEQ ID NO 11
<211> LENGTH: 17
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t
```

```
<400> SEQUENCE: 11
ccngtngtng cncargc                                                17

<210> SEQ ID NO 12
<211> LENGTH: 17
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (15)..(15)
<223> OTHER INFORMATION: n is a, c, g, or t

<400> SEQUENCE: 12
gcytgngcna cnacngg                                                17

<210> SEQ ID NO 13
<211> LENGTH: 21
<212> TYPE: DNA
<213> ORGANISM: Artificial Sequence
<220> FEATURE:
<223> OTHER INFORMATION: Primer

<400> SEQUENCE: 13
agcgggagat agtgcgggac a                                           21

<210> SEQ ID NO 14
<211> LENGTH: 24
<212> TYPE: DNA
<213> ORGANISM: Artificial Sequence
<220> FEATURE:
<223> OTHER INFORMATION: Primer

<400> SEQUENCE: 14
cagcacgccc tggacaccct gaac                                        24

<210> SEQ ID NO 15
<211> LENGTH: 24
<212> TYPE: DNA
<213> ORGANISM: Artificial Sequence
<220> FEATURE:
<223> OTHER INFORMATION: Primer

<400> SEQUENCE: 15
ggtttgggtg actgggtcgg ctgt                                        24

<210> SEQ ID NO 16
<211> LENGTH: 23
<212> TYPE: DNA
<213> ORGANISM: Artificial Sequence
<220> FEATURE:
<223> OTHER INFORMATION: Primer

<400> SEQUENCE: 16
acaaggcggt ggcagacggg aag                                         23
```

```
<210> SEQ ID NO 17
<211> LENGTH: 24
<212> TYPE: DNA
<213> ORGANISM: Artificial Sequence
<220> FEATURE:
<223> OTHER INFORMATION: Primer

<400> SEQUENCE: 17
cagcacgccc tggacaccct gaac                                          24

<210> SEQ ID NO 18
<211> LENGTH: 26
<212> TYPE: DNA
<213> ORGANISM: Artificial Sequence
<220> FEATURE:
<223> OTHER INFORMATION: Primer

<400> SEQUENCE: 18
atcaactacg cccttcttcc cgtctg                                        26

<210> SEQ ID NO 19
<211> LENGTH: 25
<212> TYPE: DNA
<213> ORGANISM: Artificial Sequence
<220> FEATURE:
<223> OTHER INFORMATION: Primer

<400> SEQUENCE: 19
aaagtagctg ttgctcgtgg cgatg                                         25

<210> SEQ ID NO 20
<211> LENGTH: 8
<212> TYPE: PRT
<213> ORGANISM: Artificial Sequence
<220> FEATURE:
<223> OTHER INFORMATION: Synthetic peptide

<400> SEQUENCE: 20

Gln Val Gly Asp Pro Val Ala Val
1               5

<210> SEQ ID NO 21
<211> LENGTH: 11
<212> TYPE: PRT
<213> ORGANISM: Artificial Sequence
<220> FEATURE:
<223> OTHER INFORMATION: Synthetic peptide

<400> SEQUENCE: 21

Thr Ala Pro Val Val Ala Gln Ala Gln Asp Leu
1               5                   10

<210> SEQ ID NO 22
<211> LENGTH: 10
<212> TYPE: PRT
<213> ORGANISM: Artificial Sequence
<220> FEATURE:
<223> OTHER INFORMATION: Synthetic peptide

<400> SEQUENCE: 22

Thr Ala Gln Ser Leu Gly Thr Tyr Thr Leu
1               5                   10

<210> SEQ ID NO 23
<211> LENGTH: 13
<212> TYPE: PRT
<213> ORGANISM: Artificial Sequence
```

```
<220> FEATURE:
<223> OTHER INFORMATION: Synthetic peptide

<400> SEQUENCE: 23

Thr Ala Asp Pro Val Thr Gln Thr Gly Asp Asp Gly Phe
1               5                   10

<210> SEQ ID NO 24
<211> LENGTH: 10
<212> TYPE: PRT
<213> ORGANISM: Artificial Sequence
<220> FEATURE:
<223> OTHER INFORMATION: Synthetic peptide

<400> SEQUENCE: 24

Asn Asp Ala Trp Asn Met Cys Ala Ser Val
1               5                   10

<210> SEQ ID NO 25
<211> LENGTH: 6
<212> TYPE: PRT
<213> ORGANISM: Artificial Sequence
<220> FEATURE:
<223> OTHER INFORMATION: Synthetic peptid

<400> SEQUENCE: 25

Met Pro Thr Phe Val Glu
1               5

<210> SEQ ID NO 26
<211> LENGTH: 7
<212> TYPE: PRT
<213> ORGANISM: Artificial Sequence
<220> FEATURE:
<223> OTHER INFORMATION: Synthetic peptide

<400> SEQUENCE: 26

Asp Thr Leu Val Ser Asn Val
1               5

<210> SEQ ID NO 27
<211> LENGTH: 8
<212> TYPE: PRT
<213> ORGANISM: Artificial Sequence
<220> FEATURE:
<223> OTHER INFORMATION: Synthetic peptide

<400> SEQUENCE: 27

Val Val Ser Thr Leu Ser Pro Thr
1               5

<210> SEQ ID NO 28
<211> LENGTH: 12
<212> TYPE: PRT
<213> ORGANISM: Artificial Sequence
<220> FEATURE:
<223> OTHER INFORMATION: Synthetic peptide

<400> SEQUENCE: 28

Gln Tyr Leu Ala Thr Ser Asn Gln Ala Asn Gln Asp
1               5                   10

<210> SEQ ID NO 29
<211> LENGTH: 13
<212> TYPE: PRT
<213> ORGANISM: Artificial Sequence
```

```
<220> FEATURE:
<223> OTHER INFORMATION: Synthetic peptide

<400> SEQUENCE: 29

Leu Asp Leu Thr Leu Ser Arg Thr Thr Thr Thr Phe Cys
1               5                   10

<210> SEQ ID NO 30
<211> LENGTH: 11
<212> TYPE: PRT
<213> ORGANISM: Artificial Sequence
<220> FEATURE:
<223> OTHER INFORMATION: Synthetic peptide

<400> SEQUENCE: 30

Glu Thr Ser Asn Gln Gln Thr Ser Ala Ala Asp
1               5                   10

<210> SEQ ID NO 31
<211> LENGTH: 12
<212> TYPE: PRT
<213> ORGANISM: Artificial Sequence
<220> FEATURE:
<223> OTHER INFORMATION: Synthetic peptide

<400> SEQUENCE: 31

Gly Val Ser Thr Leu Ser Trp Ala Thr Thr Thr Thr
1               5                   10

<210> SEQ ID NO 32
<211> LENGTH: 19
<212> TYPE: DNA
<213> ORGANISM: Artificial Sequence
<220> FEATURE:
<223> OTHER INFORMATION: Primer

<400> SEQUENCE: 32
atgcccaccg cctccatgc                                            19

<210> SEQ ID NO 33
<211> LENGTH: 179
<212> TYPE: PRT
<213> ORGANISM: Polytomella

<400> SEQUENCE: 33

Thr His Lys Tyr Phe Gln Leu Val Ser Ser Thr Ala Glu Trp Val Ala
1               5                   10                  15

Ala Arg Val Ala Pro Thr Gln Ala Phe Gln Lys Ala His Glu Ile Leu
            20                  25                  30

Arg Leu Ser Leu Asn Lys Ala Gln Glu Cys Ala Asp Pro Asp Lys Ala
        35                  40                  45

Val Lys Ile Val Tyr Asp Ser Trp Val Phe Ser Asn Ala Gln Asp
    50                  55                  60

Lys Ala Glu Lys Ile Leu Lys Ala Asp Asp Gln Val Asp Lys Val
65                  70                  75                  80

Val Ser Asn Ala His Asn Ile Tyr Gln Ala Gly Arg Ser Thr Val Asp
                85                  90                  95

Thr Ala Val Asn Asn Ile Met Glu Ile His Gln Asn Asn Ile Glu Thr
            100                 105                 110

Tyr Gln Gln Thr Ser Val Pro Val Val Ala Ser Val Leu Pro Tyr Leu
        115                 120                 125
```

```
Glu Pro Ala Ala Ala Arg Ala Phe Gln Asn Phe Arg Ser Ile His Asp
            130                 135                 140

Ser Leu Val Val Ser Pro His Tyr Lys Gln Gly Tyr Asp Met Ala Ser
145                 150                 155                 160

Ala Thr Leu Gln Trp Ala Thr Thr Thr Ser Pro Phe Arg Leu Gly Ala
                165                 170                 175

Asn Val Met

<210> SEQ ID NO 34
<211> LENGTH: 275
<212> TYPE: PRT
<213> ORGANISM: Haematococcus

<400> SEQUENCE: 34

Met Ser Glu Lys Gln Leu Lys Arg Leu Gly Phe Val His Gln Gly Ala
1               5                   10                  15

Ser Tyr Ala Tyr Ser Tyr Thr Gly Thr Ala Glu Lys Leu Tyr Lys Thr
                20                  25                  30

Ala Arg Ser Phe Ala Pro Thr Phe Val Glu Pro Thr Leu Ala Gln Val
            35                  40                  45

Glu Asp Arg Val Val Ala Ile Thr Ala Pro Val Ala Gln Ala Gln
50                  55                  60

Asp Leu Ser Glu Lys Ala Leu His Ile Ala Asp Asp Gln Val Glu Cys
65                  70                  75                  80

Ile Val Asn Thr Thr Asp Lys Ala Val Ala Asp Gly Lys Lys Gly Val
                85                  90                  95

Ile Asp Cys Met Asn Gly Val Lys Glu Met His Glu Lys Asn Met Gln
            100                 105                 110

Thr Tyr Ile Ala Thr Ser Asn Arg Tyr Phe Glu Tyr Ile Lys Gly Met
        115                 120                 125

Ser Glu Trp Ala Lys Asp Lys Met Asn Pro Ile Lys Gly Gly Gln His
130                 135                 140

Ala Leu Asp Thr Leu Asn Ala Ala Ile Ala Lys Ala Gln Glu Ala Thr
145                 150                 155                 160

Asp Pro Asp Val Ala Ala Lys Met Ala Leu Asp Ala Trp Asn Ser Phe
                165                 170                 175

Ala Ser Val Pro Val Val Ala Lys Val Leu Glu Thr Ala Asp Pro Val
            180                 185                 190

Thr Gln Thr Gly Leu Ser Ser Phe Tyr Lys Leu His Asp Thr Leu Val
        195                 200                 205

Ser Trp Pro Leu Tyr Ser Lys Val Val Ser Thr Gly Val Ser Thr Leu
210                 215                 220

Ser Trp Ala Thr Thr Thr Met Pro Tyr Lys Leu Gly Ala Gln Tyr Met
225                 230                 235                 240

Tyr Pro Leu Val Gln Pro Val Ala Asp Pro Ala Leu Ala Lys Ile Thr
                245                 250                 255

Asn Ser Lys Val Ile Asn Gly Thr Leu Ser Tyr Trp Lys Pro Thr Ala
            260                 265                 270

Ser Ala Ala
        275

<210> SEQ ID NO 35
<211> LENGTH: 267
<212> TYPE: PRT
<213> ORGANISM: Chlamydomonas
```

-continued

<400> SEQUENCE: 35

Met Ala Glu Ser Ala Gly Lys Pro Leu Lys His Leu Glu Phe Val His
1               5                   10                  15

Thr Tyr Ala His Lys Phe Ala Ser Gly Ala Ala Tyr Val Glu Gly Gly
            20                  25                  30

Tyr Gln Lys Ala Lys Thr Tyr Val Pro Ala Val Ala Gln Pro Tyr Ile
        35                  40                  45

Ala Lys Ala Glu Glu Thr Cys Leu Ala Tyr Ala Pro Leu Ala Thr Lys
50                  55                  60

Ala Thr Asp His Ala Glu Lys Ile Leu Arg Ser Thr Asp Ala Gln Leu
65                  70                  75                  80

Asp Ala Leu Tyr Ala Ala Ser Ala Ser Trp Leu Ser Ser Gln Lys
                85                  90                  95

Leu Ala Asp Ser Asn Ile Ala Ala Phe Arg Gly Ala Ala Asp Lys Tyr
            100                 105                 110

Tyr Asp Leu Val Lys Ser Thr Ala Gln His Val Thr Ser Lys Leu Pro
        115                 120                 125

Thr Asp Leu Ser Val Ala Lys Ala Arg Glu Leu Leu Ser Ala Ser Leu
    130                 135                 140

Glu Gln Ala Lys Ala Leu Ala Asp Pro Asp Ala Val Ala Ala
145                 150                 155                 160

Leu Asp Ala Trp Thr Lys Phe Ala Ala Ile Pro Ala Val Ala Lys Val
                165                 170                 175

Leu Ser Ala Ala Ser Pro Leu Thr Gly Lys Gly Val Ala Ala Phe Thr
            180                 185                 190

Ala Ala His Asp Leu Leu Val His Ser Ala Leu Tyr Arg Tyr Gly Val
        195                 200                 205

Ser Val Gly Ala Ser Thr Leu Gly Trp Ala Thr Ser Thr Thr Pro Tyr
    210                 215                 220

Lys Leu Ser Ala Ala Tyr Leu Tyr Pro Leu Val Gln Pro Val Ala Asp
225                 230                 235                 240

Pro Ala Leu Asp Lys Val Ser Lys Ser Thr Tyr Val Asn Ala Ala Ile
                245                 250                 255

Lys Tyr Trp Ala Pro Ala Pro Val Ala Ala Ala
            260                 265

<210> SEQ ID NO 36
<211> LENGTH: 242
<212> TYPE: PRT
<213> ORGANISM: Volvox

<400> SEQUENCE: 36

Met Ala Asp Asp Arg Lys Leu Lys Arg Leu Gly Phe Val Asp Ala Tyr
1               5                   10                  15

Thr His Lys Leu Ala Asn Gly Ala Ala Tyr Val Glu Gly Ala Tyr Lys
            20                  25                  30

Lys Val Lys Pro Leu Val Pro Gln Gln Val Gln Pro Phe Leu Ala Lys
        35                  40                  45

Val Glu Asp Ala Val Leu Ala Tyr Thr Ala Pro Val Ala Lys Ala
50                  55                  60

Ser Asp Gln Ala Glu Lys Phe Leu Arg Ile Thr Asp Glu Gln Val Asp
65                  70                  75                  80

Tyr Leu Tyr Val Glu Thr Ala Ala Tyr Leu Thr Gln Thr Arg Lys Leu
            85                  90                  95

-continued

```
Thr Gln Ser Asn Ile Asp Thr Phe Arg Ser Ala Ala Asp Lys Tyr Tyr
            100             105             110

Gln Met Val Lys Ser Thr Ala Asp Tyr Leu Ala Ser Lys Leu Ser Tyr
        115             120             125

Asp Ile Ser Val Gln Ala Ala Arg Asp Phe Ile Ser Lys Ser Val Glu
        130             135             140

Lys Ala Lys Glu Leu Ser Asp Pro Asp Ala Ala Val Arg Ile Val Tyr
145                 150             155             160

Asp Ser Trp Gln Gln Phe Ala Ala Ile Pro Ala Val Ala Lys Thr Leu
                165             170             175

Glu Lys Thr Ala Pro Val Thr Arg Lys Gly Phe Glu Thr Phe Ile Ala
            180             185             190

Ala His Asp Ala Leu Val Ser Ser Leu Val Tyr Lys Arg Ser Val Ser
        195             200             205

Leu Gly Ala Thr Thr Leu Gly Trp Ala Thr Thr Thr Thr Pro Tyr Lys
        210             215             220

Leu Gly Ala Gln Tyr Leu Tyr Pro Met Val Gln Ser Val Ala Asp Pro
225             230             235             240

Ala Leu
```